United States Patent
Naito

(10) Patent No.: US 8,915,841 B2
(45) Date of Patent: Dec. 23, 2014

(54) ENDOSCOPIC SYSTEM

(75) Inventor: Kimihiko Naito, Kawasaki (JP)

(73) Assignee: Olympus Medical Systems Corp., Tokyo (JP)

(*) Notice: Subject to any disclaimer, the term of this patent is extended or adjusted under 35 U.S.C. 154(b) by 45 days.

(21) Appl. No.: 13/213,844

(22) Filed: Aug. 19, 2011

(65) Prior Publication Data

US 2012/0046522 A1 Feb. 23, 2012

Related U.S. Application Data

(63) Continuation of application No. PCT/JP2010/069311, filed on Oct. 29, 2010.

(30) Foreign Application Priority Data

Mar. 17, 2010 (JP) ................................ 2010-061588

(51) Int. Cl.
*A61B 1/00* (2006.01)
*A61B 1/005* (2006.01)
*A61B 1/002* (2006.01)
*A61B 5/06* (2006.01)

(52) U.S. Cl.
CPC ............. *A61B 1/0052* (2013.01); *A61B 1/0057* (2013.01); *A61B 1/002* (2013.01); *A61B 1/00057* (2013.01); *A61B 5/062* (2013.01); *A61B 1/00006* (2013.01)
USPC .............................. 600/145; 600/146; 600/149

(58) Field of Classification Search
CPC .... A61B 1/005; A61B 1/0051; A61B 1/0057; A61B 2017/003; A61M 25/0147
USPC ......... 600/145, 146, 104, 139, 114, 117, 144, 600/149, 424, 585, 101; 606/33, 108, 129, 606/1, 46, 78; 604/523, 525, 528, 95.04, 604/510, 95.01; 138/118
See application file for complete search history.

(56) References Cited

U.S. PATENT DOCUMENTS 4,688,555 A * 8/1987 Wardle .......................... 600/149
5,060,632 A * 10/1991 Hibino et al. .................. 600/109
(Continued)

FOREIGN PATENT DOCUMENTS

CN 101115432 A 1/2008
CN 101227854 A 7/2008
(Continued)

OTHER PUBLICATIONS

International Search Report issued in Application No. PCT/JP2010/069311; Dated Dec. 28, 2010 (With Translation).
(Continued)

*Primary Examiner* — John P Leubecker
*Assistant Examiner* — Ronald D Colque
(74) *Attorney, Agent, or Firm* — Oliff PLC

(57) ABSTRACT

An endoscopic system includes an insertion-section, a wire, an adjustment-unit, a memory, a shape-acquiring-unit and a controller. The insertion-section includes a tubular-section and a bending-section. The wire is inserted in the insertion-section and pulled and loosened to bend the bending-section. The adjustment-unit adjusts tensile force applied to the wire. The memory stores correspondent information including a relationship between increase/decrease information indicative of increase/decrease in the tensile force due to a shape of the tubular-section and shape information indicative of the shape of the tubular-section. The shape-acquiring-unit acquires the shape of the tubular-section. The controller obtains the increase/decrease information corresponding to the shape information acquired by the shape-acquiring-unit with reference to the correspondent information, generates an adjustment signal configured to drive the adjustment-unit based on the increase/decrease information, and outputs the adjustment signal to the adjustment-unit.

12 Claims, 19 Drawing Sheets

(56) References Cited

U.S. PATENT DOCUMENTS

| | | | | |
|---|---|---|---|---|
| 5,299,559 | A * | 4/1994 | Bruce et al. | 600/141 |
| 5,462,527 | A * | 10/1995 | Stevens-Wright et al. | 604/528 |
| 5,531,664 | A * | 7/1996 | Adachi et al. | 600/149 |
| 5,624,380 | A * | 4/1997 | Takayama et al. | 600/146 |
| 5,885,208 | A * | 3/1999 | Moriyama | 600/144 |
| 6,432,041 | B1 * | 8/2002 | Taniguchi et al. | 600/118 |
| 6,511,417 | B1 | 1/2003 | Taniguchi et al. | |
| 6,589,163 | B2 * | 7/2003 | Aizawa et al. | 600/118 |
| 7,413,543 | B2 * | 8/2008 | Banik et al. | 600/129 |
| 8,268,009 | B2 * | 9/2012 | Teitelbaum et al. | 623/23.64 |
| 2002/0188174 | A1 | 12/2002 | Aizawa et al. | 600/118 |
| 2003/0055317 | A1 | 3/2003 | Taniguchi et al. | |
| 2003/0195432 | A1 * | 10/2003 | Kortenbach et al. | 600/562 |
| 2004/0092892 | A1 * | 5/2004 | Kagan et al. | 604/264 |
| 2004/0158124 | A1 * | 8/2004 | Okada | 600/104 |
| 2004/0193015 | A1 | 9/2004 | Ikeda et al. | |
| 2004/0199052 | A1 * | 10/2004 | Banik et al. | 600/142 |
| 2005/0033285 | A1 * | 2/2005 | Swanson et al. | 606/41 |
| 2005/0075538 | A1 * | 4/2005 | Banik et al. | 600/141 |
| 2005/0096750 | A1 * | 5/2005 | Kagan et al. | 623/23.65 |
| 2005/0119527 | A1 * | 6/2005 | Banik et al. | 600/117 |
| 2005/0131279 | A1 * | 6/2005 | Boulais et al. | 600/141 |
| 2005/0154262 | A1 * | 7/2005 | Banik et al. | 600/179 |
| 2005/0197536 | A1 * | 9/2005 | Banik et al. | 600/179 |
| 2005/0222499 | A1 * | 10/2005 | Banik et al. | 600/132 |
| 2005/0240279 | A1 * | 10/2005 | Kagan et al. | 623/23.65 |
| 2005/0245789 | A1 * | 11/2005 | Smith et al. | 600/159 |
| 2007/0106114 | A1 * | 5/2007 | Sugimoto et al. | 600/117 |
| 2007/0112255 | A1 | 5/2007 | Ikeda et al. | |
| 2007/0173694 | A1 * | 7/2007 | Tsuji et al. | 600/146 |
| 2007/0249897 | A1 * | 10/2007 | Miyamoto et al. | 600/104 |
| 2008/0051631 | A1 * | 2/2008 | Dejima et al. | 600/141 |
| 2008/0064921 | A1 * | 3/2008 | Larkin et al. | 600/104 |
| 2008/0064927 | A1 * | 3/2008 | Larkin et al. | 600/114 |
| 2008/0065100 | A1 * | 3/2008 | Larkin | 606/130 |
| 2008/0086029 | A1 * | 4/2008 | Uchiyama et al. | 600/114 |
| 2008/0221592 | A1 * | 9/2008 | Kawai | 606/130 |
| 2008/0243176 | A1 * | 10/2008 | Weitzner et al. | 606/206 |
| 2008/0255422 | A1 * | 10/2008 | Kondoh et al. | 600/141 |
| 2008/0255423 | A1 * | 10/2008 | Kondo et al. | 600/146 |
| 2008/0255505 | A1 * | 10/2008 | Carlson et al. | 604/95.04 |
| 2008/0306339 | A1 * | 12/2008 | Hashimoto et al. | 600/114 |
| 2009/0143642 | A1 | 6/2009 | Takahashi et al. | |
| 2009/0227841 | A1 * | 9/2009 | Miyako et al. | 600/139 |
| 2010/0022827 | A1 * | 1/2010 | Naito | 600/104 |
| 2010/0076263 | A1 * | 3/2010 | Tanaka et al. | 600/109 |
| 2010/0204547 | A1 | 8/2010 | Tanaka et al. | |
| 2010/0249506 | A1 * | 9/2010 | Prisco | 600/117 |
| 2010/0249507 | A1 * | 9/2010 | Prisco et al. | 600/117 |

FOREIGN PATENT DOCUMENTS

| | | | | |
|---|---|---|---|---|
| CN | 101444415 | A | | 6/2009 |
| CN | 101652092 | A | | 2/2010 |
| EP | 1 849 396 | A1 | | 10/2007 |
| JP | A-4-2320 | | | 1/1992 |
| JP | A-06-217926 | | | 8/1994 |
| JP | A-08-224241 | | | 9/1996 |
| JP | A-2000-079087 | | | 3/2000 |
| JP | A-2000-300511 | | | 10/2000 |
| JP | A-2003-061968 | | | 3/2003 |
| JP | A-2003-230536 | | | 8/2003 |
| JP | A-2007-029290 | | | 2/2007 |
| JP | A-2009-131374 | | | 6/2009 |
| WO | WO 2008155828 | A1 * | 12/2008 | 600/145 |
| WO | WO 2009/069395 | A1 | | 6/2009 |

OTHER PUBLICATIONS

Nov. 2, 2012 Supplementary European Search Report issued in European Application No. 10 84 7975.
International Preliminary Report on Patentability issued in International Application No. PCT/JP2010/069311 mailed on Nov. 1, 2012.
Written Opinion of the International Searching Authority issued in International Application No. PCT/JP2010/069311 mailed on Dec. 28, 2010 (translation only).
May 19, 2014 Office Action issued in Application No. 201080064751.X (with English Translation).

* cited by examiner

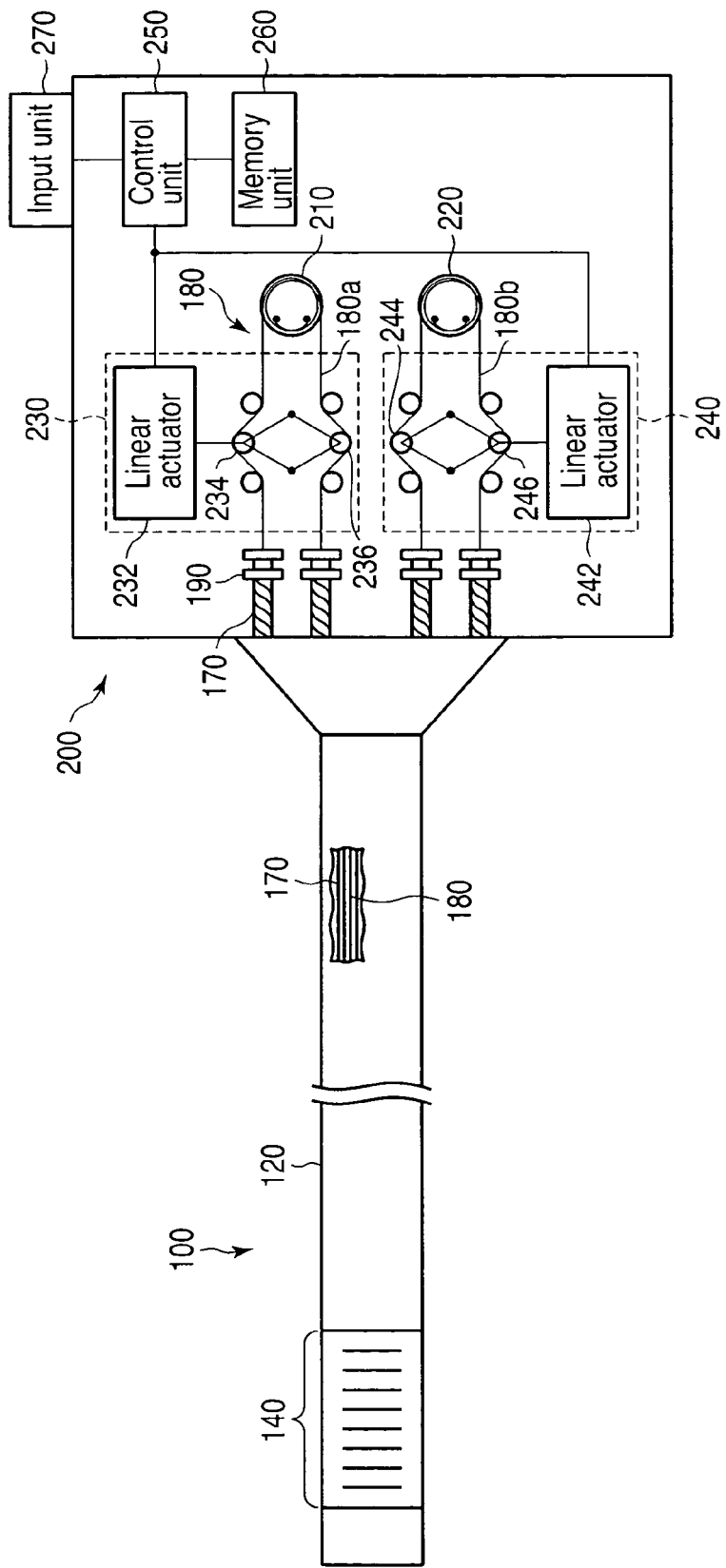
F I G. 1

| | RL adjustment value | UD adjustment value |
|---|---|---|
| Reversal (small) mode | -2 | -10 |
| Reversal (large) mode | -4 | -5 |
| Large intestine mode | +3 | -7 |
| ⋮ | ⋮ | ⋮ |

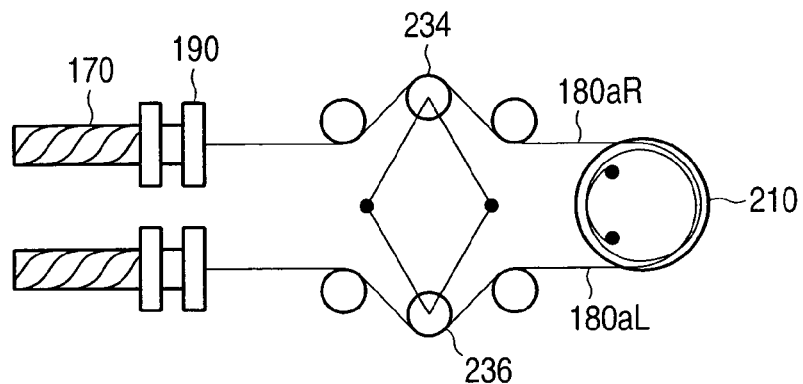
F I G. 6A
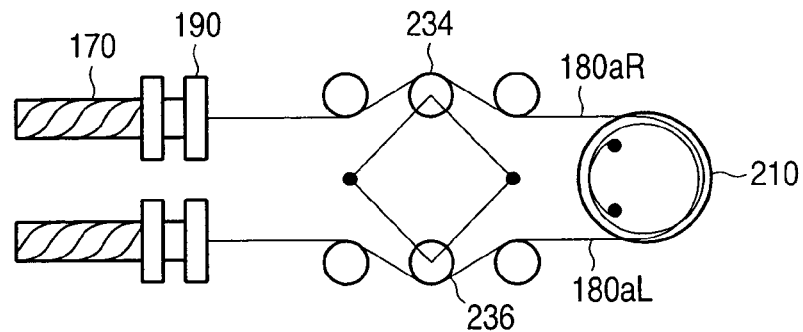
F I G. 6B
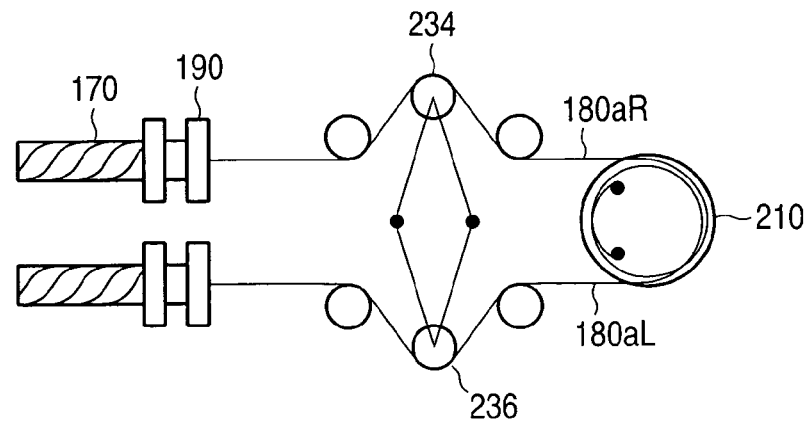
F I G. 6C

```
      ┌─────────┐
      │  Start  │
      └────┬────┘
           ▼
  ┌──────────────────┐
  │ Acquire moving   │── S21
  │ distance of      │
  │ second angle wire│
  └────────┬─────────┘
           ▼
  ┌──────────────────┐
  │ Read adjustment  │── S22
  │ value            │
  └────────┬─────────┘
           ▼
  ┌──────────────────┐
  │ Calculate drive  │── S23
  │ amount of tensile│
  │ force adjustment │
  │ unit             │
  └────────┬─────────┘
           ▼
  ┌──────────────────┐
  │ Control drive of │── S24
  │ tensile force    │
  │ adjustment unit  │
  └────────┬─────────┘
           ▼
       ┌───────┐
       │  End  │
       └───────┘
```

F I G. 10

| Moving distance of second angle wire | Adjustment value for first angle wire |
|---|---|
| ⋮ | ⋮ |
| -3 | -7 |
| -2 | -3 |
| -1 | -1 |
| 0 | 0 |
| +1 | +1 |
| +2 | +3 |
| +3 | +7 |
| ⋮ | ⋮ |

F I G. 11

|  | | Moving distance of UD angle wire of endoscope | | | | | | | |
|---|---|---|---|---|---|---|---|---|---|
|  |  | ... | -3 | -2 | -1 | 0 | +1 | +2 | +3 | ... |
| Moving distance of RL angle wire of endoscope | ... | ... | ... | ... | ... | ... | ... | ... | ... | ... |
| | -3 | ... | -9<br>-8 | -8<br>-3 | -6<br>-1 | -6<br>0 | -6<br>+1 | -8<br>+3 | -9<br>+8 | ... |
| | -2 | ... | -4<br>-7 | -3<br>-3 | -3<br>-1 | -3<br>0 | -3<br>+1 | -3<br>+3 | -4<br>+7 | ... |
| | -1 | ... | -1<br>-7 | -1<br>-3 | -1<br>-1 | -1<br>0 | -1<br>+1 | -1<br>+3 | -1<br>+7 | ... |
| | 0 | ... | 0<br>-7 | 0<br>-3 | 0<br>-1 | 0<br>0 | 0<br>+1 | 0<br>+3 | 0<br>+7 | ... |
| | +1 | ... | +1<br>-7 | +1<br>-3 | +1<br>-1 | +1<br>0 | +1<br>+1 | +1<br>+3 | +1<br>+7 | ... |
| | +2 | ... | +4<br>-7 | +3<br>-3 | +3<br>-1 | +3<br>0 | +3<br>+1 | +3<br>+3 | +4<br>+7 | ... |
| | +3 | ... | +9<br>-8 | +8<br>-3 | +6<br>-1 | +6<br>0 | +6<br>+1 | +8<br>+3 | +9<br>+8 | ... |
| | ... | ... | ... | ... | ... | ... | ... | ... | ... | ... |

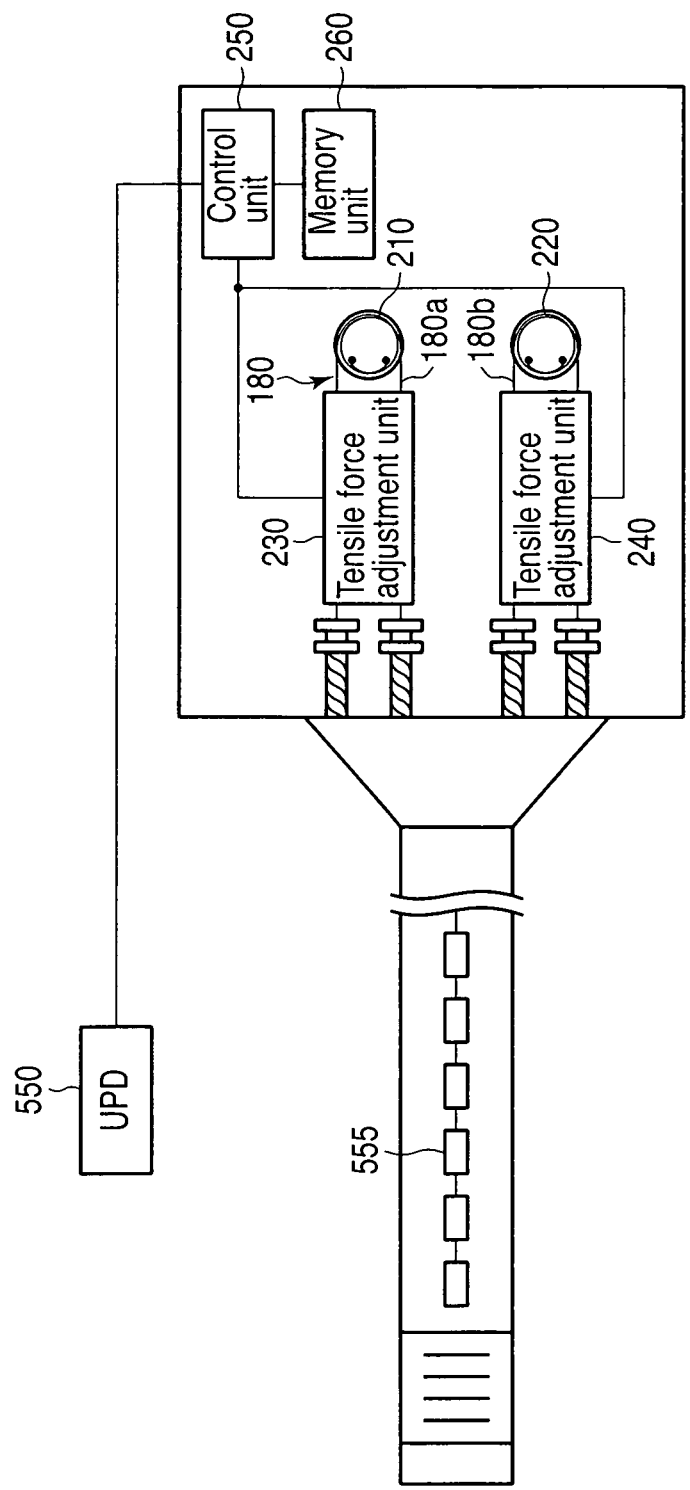
F I G. 15

| | Bending amount of bending section in UD direction | | | | | | | |
|---|---|---|---|---|---|---|---|---|
| | ... | -3 | -2 | -1 | 0 | +1 | +2 | +3 | ... |
| Bending amount of bending section in RL direction | ... | ... | ... | ... | ... | ... | ... | ... | ... |
| -3 | ... | -9<br>-8 | -8<br>-3 | -6<br>-1 | -6<br>0 | -6<br>+1 | -8<br>+3 | -9<br>+8 | ... |
| -2 | ... | -4<br>-7 | -3<br>-3 | -3<br>-1 | -3<br>0 | -3<br>+1 | -3<br>+3 | -4<br>+7 | ... |
| -1 | ... | -1<br>-7 | -1<br>-3 | -1<br>-1 | -1<br>0 | -1<br>+1 | -1<br>+3 | -1<br>+7 | ... |
| 0 | ... | 0<br>-7 | 0<br>-3 | 0<br>-1 | 0<br>0 | 0<br>+1 | 0<br>+3 | 0<br>+7 | ... |
| +1 | ... | +1<br>-7 | +1<br>-3 | +1<br>-1 | +1<br>0 | +1<br>+1 | +1<br>+3 | +1<br>+7 | ... |
| +2 | ... | +4<br>-7 | +3<br>-3 | +3<br>-1 | +3<br>0 | +3<br>+1 | +3<br>+3 | +4<br>+7 | ... |
| +3 | ... | +9<br>-8 | +8<br>-3 | +6<br>-1 | +6<br>0 | +6<br>+1 | +8<br>+3 | +9<br>+8 | ... |
| | ... | ... | ... | ... | ... | ... | ... | ... | ... |

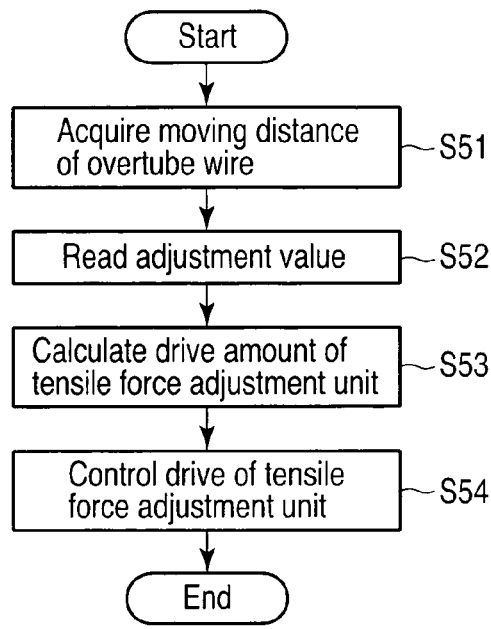
F I G. 19
| | Moving distance of UD angle wire of overtube | | | | | | | | |
|---|---|---|---|---|---|---|---|---|---|
| | | ... | -3 | -2 | -1 | 0 | +1 | +2 | +3 | ... |
| Moving distance of RL angle wire of overtube | ... | ... | ... | ... | ... | ... | ... | ... | ... | ... |
| | -3 | ... | -9<br>-8 | -8<br>-3 | -6<br>-1 | -6<br>0 | -6<br>+1 | -8<br>+3 | -9<br>+8 | ... |
| | -2 | ... | -4<br>-7 | -3<br>-3 | -3<br>-1 | -3<br>0 | -3<br>+1 | -3<br>+3 | -4<br>+7 | ... |
| | -1 | ... | -1<br>-7 | -1<br>-3 | -1<br>-1 | -1<br>0 | -1<br>+1 | -1<br>+3 | -1<br>+7 | ... |
| | 0 | ... | 0<br>-7 | 0<br>-3 | 0<br>-1 | 0<br>0 | 0<br>+1 | 0<br>+3 | 0<br>+7 | ... |
| | +1 | ... | +1<br>-7 | +1<br>-3 | +1<br>-1 | +1<br>0 | +1<br>+1 | +1<br>+3 | +1<br>+7 | ... |
| | +2 | ... | +4<br>-7 | +3<br>-3 | +3<br>-1 | +3<br>0 | +3<br>+1 | +3<br>+3 | +4<br>+7 | ... |
| | +3 | ... | +9<br>-8 | +8<br>-3 | +6<br>-1 | +6<br>0 | +6<br>+1 | +8<br>+3 | +9<br>+8 | ... |
| | ... | ... | ... | ... | ... | ... | ... | ... | ... | ... |
F I G. 20

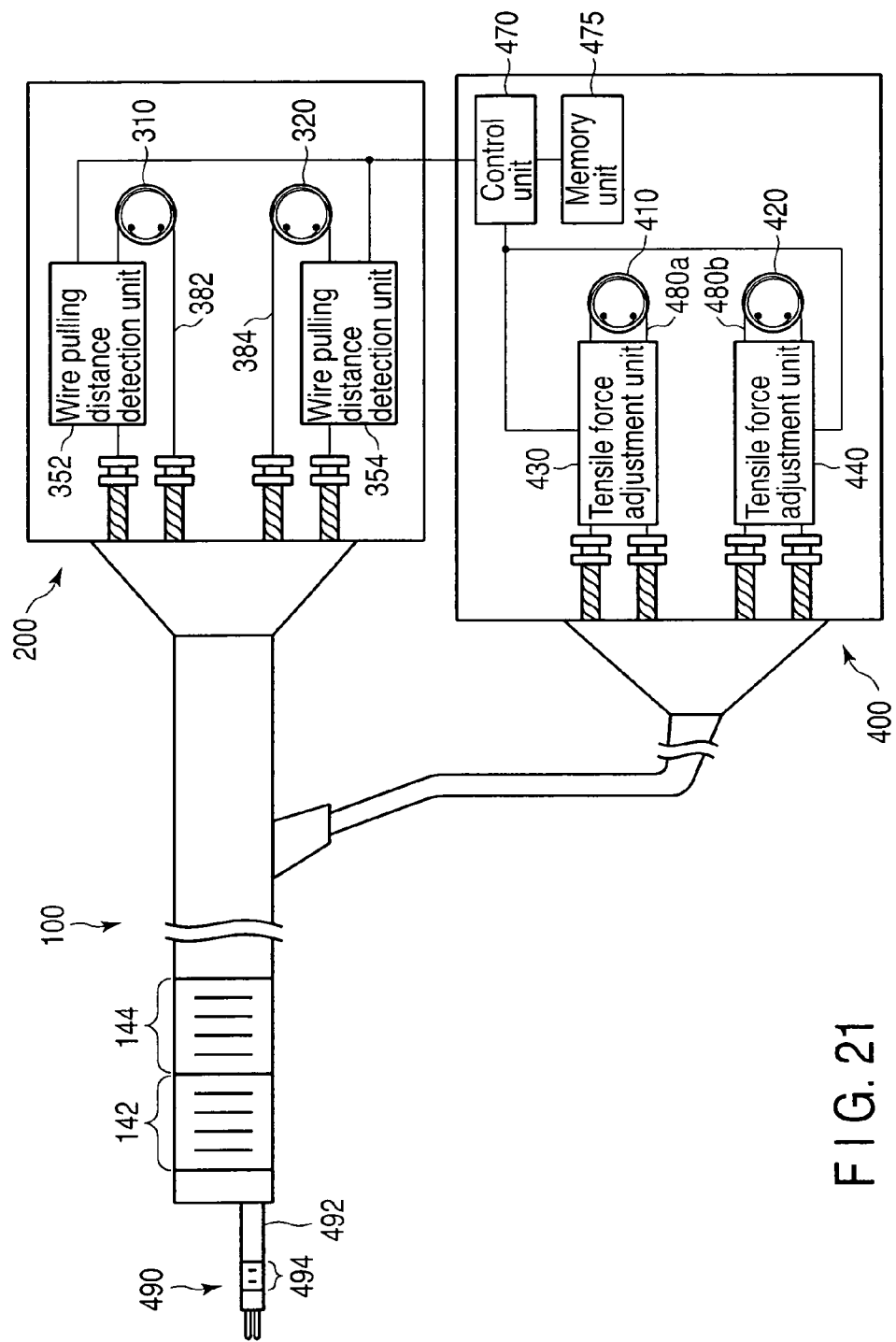
F I G. 21

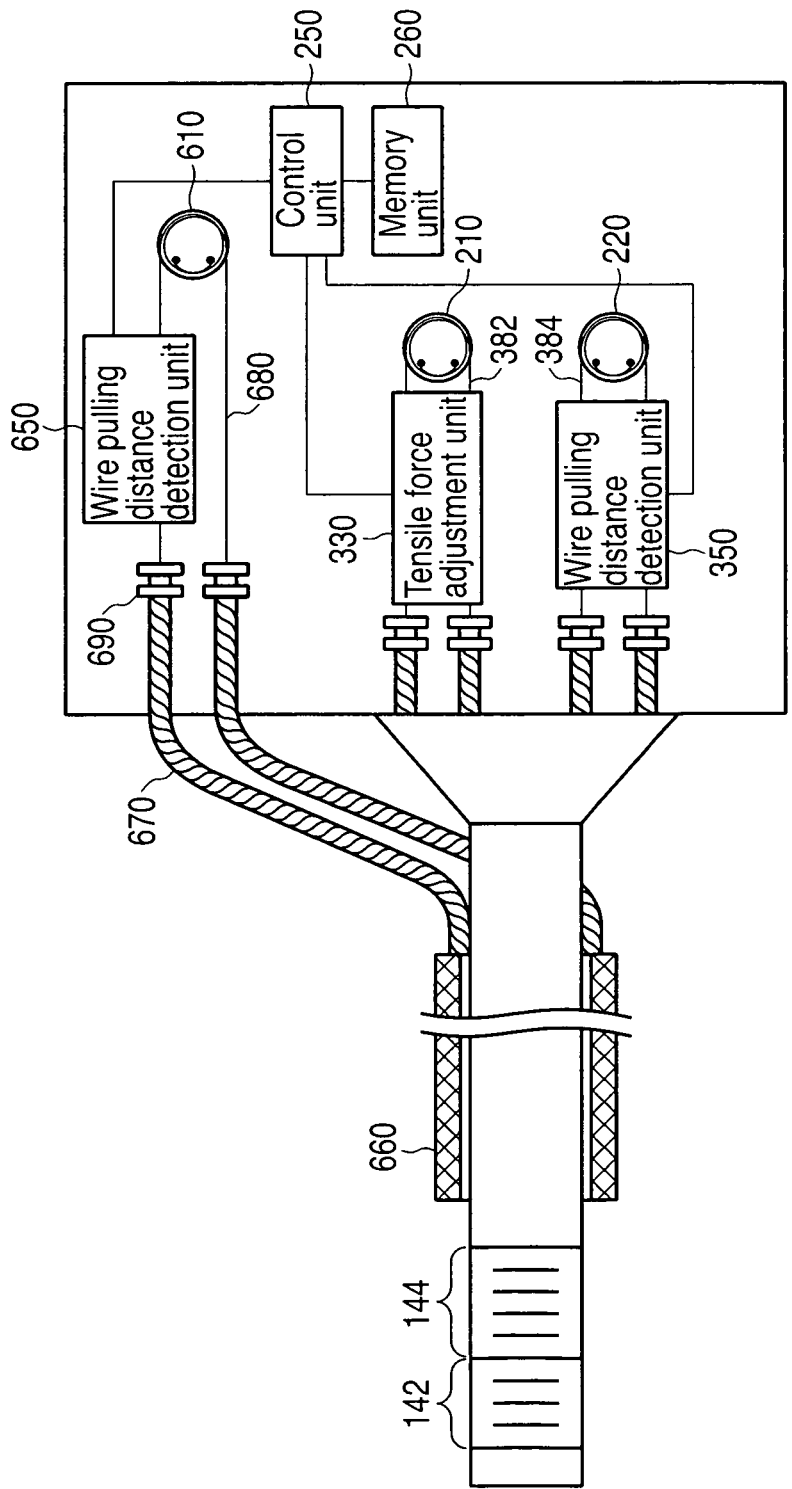
F I G. 23

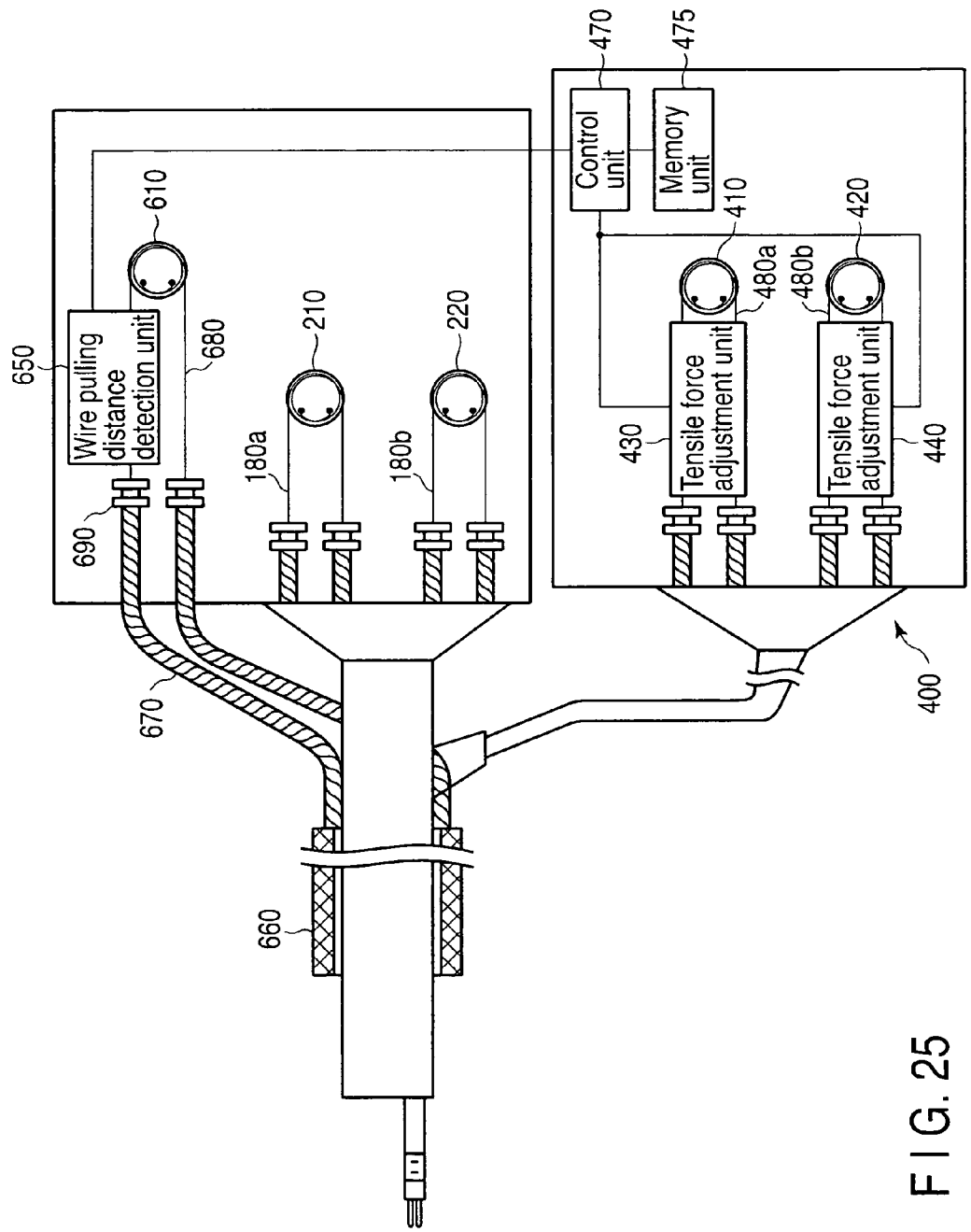
F I G. 25

ENDOSCOPIC SYSTEM

CROSS REFERENCE TO RELATED APPLICATIONS

This is a Continuation Application of PCT Application No. PCT/JP2010/069311, filed Oct. 29, 2010, which was published under PCT Article 21(2) in Japanese.

This application is based upon and claims the benefit of priority from prior Japanese Patent Application No. 2010-061588, filed Mar. 17, 2010, the entire contents of which are incorporated herein by reference.

BACKGROUND OF THE INVENTION

1. Field of the Invention

The present invention relates to an endoscopic system comprising a bending flexible tube section and a bending section.

2. Description of the Related Art

In general, an endoscope includes an elongated insertion section that is inserted into a subject and an operating section that is connected to a proximal end side of the insertion section. Further, the insertion section has an elongated flexible tube section having flexibility and a bending section that is provided on a distal end side of the flexible tube section and operated to bend. The bending section has a bending tube having a configuration that node rings are aligned in the longitudinal direction of the insertion section and coupled through joints capable of swinging. To operate the bending section to bend, a pair of wires having one end coupled with each bending tube is arranged in the insertion section. The other end of the pair of wires is fixed to a pulley coupled with a bending operation knob of the operating section. When the bending operation knob is rotated, the pulley is rotated on an axis, and one of the pair of wires is taken up, and the other is veered out. When the wires are taken up and veered out (pulled and loosened), the bending section is operated to bend. Further, when the two pulleys each having such a bending mechanism are provided, the bending section can be operated to bend in both a right-left direction and an up-down direction. Based on a combination of these bending directions, the bending section can bend in arbitrary directions. For example, Jpn. Pat. Appln. KOKAI Publication No. 8-224241 discloses a medical manipulator comprising such a bending mechanism.

BRIEF SUMMARY OF THE INVENTION

According to an aspect of the invention, an endoscopic system includes an insertion section including a flexible elongated tubular section and a bendable bending section; a wire which is inserted in the insertion section and pulled and loosened to bend the bending section; an adjustment unit which adjusts tensile force applied to the wire; a memory unit which stores correspondent information including a relationship between increase/decrease information indicative of increase/decrease in the tensile force due to a shape of the tubular section and shape information indicative of the shape of the tubular section; a shape acquiring unit which acquires the shape of the tubular section as the shape information; and a control unit which obtains the increase/decrease information corresponding to the shape information acquired by the shape acquiring unit based on the shape information acquired by the shape acquiring unit with reference to the correspondent information stored in the memory unit, generates an adjustment signal configured to drive the adjustment unit based on the increase/decrease information to adjust the tensile force, and outputs the adjustment signal to the adjustment unit.

According to another aspect of the invention, an endoscopic system includes a flexible elongated endoscope insertion section; a manipulator which is inserted in the endoscope insertion section along a longitudinal direction of the endoscope insertion section to protrude from a distal end of the endoscope insertion section, and includes a manipulator bending section and a flexible elongated manipulator tubular section; a manipulator wire which is inserted in the manipulator tubular section and transmits power that bends the manipulator bending section; a manipulator adjustment unit which adjusts tensile force applied to the manipulator wire; a memory unit which stores correspondent information including a relationship between increase/decrease information indicative of increase/decrease in the tensile force due to a shape of the manipulator tubular section and shape information indicative of the shape of the manipulator tubular section; a manipulator shape acquiring unit which acquires the shape of the manipulator tubular section as the shape information; and a control unit which obtains the increase/decrease information corresponding to the shape information acquired by the manipulator shape acquiring unit based on the shape information acquired by the manipulator shape acquiring unit with reference to the correspondent information stored in the memory unit, generates an adjustment signal configured to drive the manipulator adjustment unit based on the increase/decrease information to adjust the tensile force, and outputs the adjustment signal to the manipulator adjustment unit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram schematically showing an example of a configuration of an endoscopic system according to a first embodiment of the present invention;

FIG. 6A is a diagram showing a reference state for explaining an example of a mechanism of a tensile force adjustment unit in the endoscopic system according to the first embodiment of the present invention;

FIG. 6B is a diagram showing a state where paths of the angle wires are shortened for explaining an example of the mechanism of the tensile force adjustment unit in the endoscopic system according to the first embodiment of the present invention;

FIG. 6C is a diagram showing a state where paths of the angle wires are increased for explaining an example of the mechanism of the tensile force adjustment unit in the endoscopic system according to the first embodiment of the present invention;

FIG. 10 is a flowchart for explaining an example of processing in a control unit in the endoscopic system according to the second embodiment of the present invention;

FIG. 11 is a diagram showing an example of information stored in a memory unit of the endoscopic system according to the second embodiment of the present invention;

FIG. 15 is a diagram schematically showing an example of a configuration of an endoscopic system according to a fourth embodiment of the present invention;

FIG. 19 is a flowchart for explaining an example of processing in a control unit of the endoscopic system according to the fifth embodiment of the present invention;

FIG. 20 is a diagram showing an example of information stored in a memory unit of the endoscopic system according to the fifth embodiment of the present invention;

FIG. 21 is a diagram schematically showing an example of a configuration of an endoscopic system according to an embodiment that is a combination of the second embodiment and the third embodiment of the present invention;

FIG. 23 is a diagram schematically showing an example of a configuration of an endoscopic system according to an embodiment that is a combination of the second embodiment and the fifth embodiment of the present invention;

FIG. 25 is a diagram schematically showing an example of a configuration of an endoscopic system according to an embodiment that is a combination of the third embodiment and the fifth embodiment of the present invention.

DETAILED DESCRIPTION OF THE INVENTION

[First Embodiment]

Figure 2A:
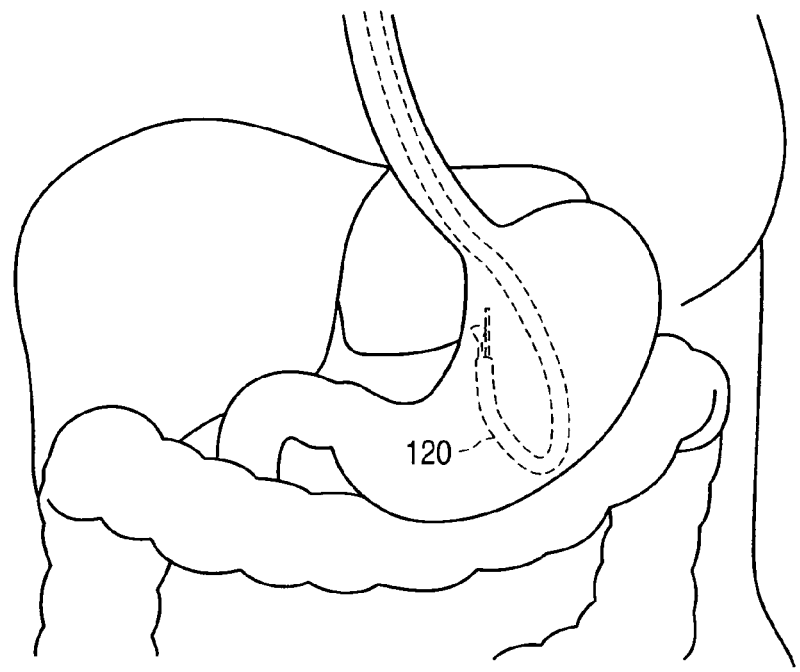
FIG. 2A is a schematic view showing an example of a shape of an insertion section when using the endoscopic system according to the first embodiment of the present invention in case of bending a flexible tube section into a J-like shape in a stomach.

A first embodiment according to the present invention will be first described with reference to the drawings. An endoscopic system according to this embodiment stores pieces of information concerning a bent state of an insertion section in response to respective operative procedures when the insertion section is inserted into a subject, for example, when the insertion section is bent into a J-like shape in a stomach or it approaches a gallbladder through the stomach in natural orifice transluminal endoscopic surgery (NOTES). This endoscopic system adjusts tensile force of angle wires that are used for transmitting drive force to a bending section installed at a distal end of the insertion section in a body based on the appropriately selected information concerning the bent state of the insertion section.

FIG. 1 shows an outline of an overall configuration of the endoscopic system according to this embodiment. This endoscopic system has an insertion section 100 that is inserted into a subject and has an elongated shape and an operating section 200 used by an operator to perform various kinds of operations of this endoscopic system outside the subject.

The insertion section 100 comprises an elongated flexible tube section 120 having flexibility and a bending section 140 coupled with a distal end of the flexible tube section 120. The flexible tube section 120 includes a metallic helical tube, a reticular tube provided on an outer peripheral side of the helical tube, and a resin envelope that covers an outer peripheral surface of the reticular tube. The bending section 140 has a bending tube that is formed by aligning cylindrical node rings in the longitudinal direction of the bending section 140 and coupling the node rings through joints capable of swinging, a reticular tube provided on the outer peripheral side of the bending tube, and a resin envelop that covers an outer peripheral surface of the reticular tube.

Four coil pipes 170 are disposed to penetrate the flexible tube section 120 and the bending section 140 in the longitudinal direction, and angle wires 180 are inserted in these coil pipes 170. In the operating section 200, one end of each coil pipe 170 arranged in the insertion section 100 is fixed by a coil receiver.

First and second angle wires 180 forming a pair connect an RL angle pulley 210 to one node ring in the bending section 140. Specifically, one end of the first angle wire 180 is wound around and fixed to the RL angle pulley 210, and the other end is fixed to the node ring through one of the four coil pipes 170. Likewise, the second angel wire 180 is wound around and fixed to the RL angle pulley 210 in an opposite direction of the winding direction of the first angle wire 180, and the other end of the same is inserted into the coil pipe 170 and fixed to the same node ring. Furthermore, each of third and fourth angle wires 180 forming the other pair has one end likewise wound around and fixed to an UD angle pulley 220 and the other end inserted into the coil pipe 170 and fixed to the node ring in the bending section 140.

Based on such a configuration, when an operator rotates a non-illustrated operation knob coupled with the RL angle pulley 210, the RL angle pulley 210 is rotated, and one of the RL angle wires 180 is pulled, and the other of the same is veered out. As a result, the node ring which is connected with the angle wires 180 fixed to the bending section 140 is pulled, the joint oscillates, and the bending section 140 freely bends in a right-left direction. Likewise, when the operator rotates a non-illustrated operation knob coupled with the UD angle pulley 220, the UD angle pulley 220 rotates, the angle wires 180 for the UD angle are pulled and loosened, and the bending section 140 bends in an up-down direction. In this embodiment, an example of bending the bending section 140 in two axial directions perpendicular to each other, i.e., the up-down direction and the right-left direction by using the two joints will be explained, but the bending section can bent in multiaxial directions by using more joints.

In the following description, the pair of angle wires used for bending the bending section 140 in the right-left direction will be referred to as RL angle wires 180*a*, and the pair of angle wires used for bending the bending section 140 in the up-down direction will be referred to as UD angle wires 180*b*.

An RL tensile force adjustment unit 230 and an UD tensile force adjustment unit 240 are arranged between coil receivers 190 and the RL angle pulley 210 and between the coil receivers 190 and the UD angle pulley 220, respectively. The RL tensile force adjustment unit 230 has a linear actuator 232, a movable pulley 234, and a movable pulley 236. When the movable pulley 234 moves in response to driving of the linear actuator 232, tensile force of the RL angle wire 180*a* wound around the movable pulley 234 varies. Likewise, the UD tensile force adjustment unit 240 has a linear actuator 242, a movable pulley 244, and a movable pulley 246 to change tensile force of the UD angle wire 180*b*.

The operating section 200 has a control unit 250, a memory unit 260, and an input unit 270. The input unit 270 is a unit that accepts instructions from an operator. The input unit 270 outputs instructions received from the operator to the control unit 250. The memory unit 260 stores information required for arithmetic operations performed by the control unit 250 and outputs required information to the control unit 250 in response to a request from the control unit 250. The control unit 250 reads out required information from the memory unit 260 based on an instruction from the operator input from the input unit 270 and executes an arithmetic operation by using this required information to calculate a value concerning adjustment of the angle wires 180. Furthermore, the control unit 250 controls operations of the linear actuator 232 and the linear actuator 242 based on the calculated adjustment value.

In this manner, the bending section 140 functions as, e.g., a bending section provided in the elongated flexible insertion section, the angle wires 180 function as, e.g., wires that are pulled or loosened to bend the bending section, the memory unit 260 functions as, e.g., a memory unit that stores information indicative of a relationship between a shape of the insertion section and an adjustment value for driving an adjustment unit in case of this shape of the insertion section, the RL tensile force adjustment unit 230 and the UD tensile force adjustment unit 240 function as, e.g., adjustment units that adjust tensile force applied to the wires, the control unit 250 functions as, e.g., a control unit that determines an adjustment value and controls the adjustment units based on the adjustment value, and the input unit 270 functions as, e.g., an input unit that acquires a procedure mode in accordance with a procedure using the endoscopic system.

An operation of the endoscopic system according to this embodiment will now be described with reference to the drawings.

Various conformations of this endoscopic system can be considered in accordance with use statuses. Like a loop shape indicated by a broken line in FIG. 2A, the flexible tube section 120 may be bent with a relatively small curvature in such a manner that the flexible tube section 120 is bent into a J-like shape in, e.g., a digestive tract such as a stomach. Further, like a loop shape indicated by a solid line in FIG. 2B, in the natural orifice transluminal endoscopic surgery (NOTES), it is also possible to consider a situation that the flexible tube section 120 is bent with a relatively large curvature to approach a gallbladder through the stomach. Besides, approaching a non-illustrated sigmoid colon, a descending colon, a transverse colon, an ascending colon, and others can be also considered.

Figure 3A:
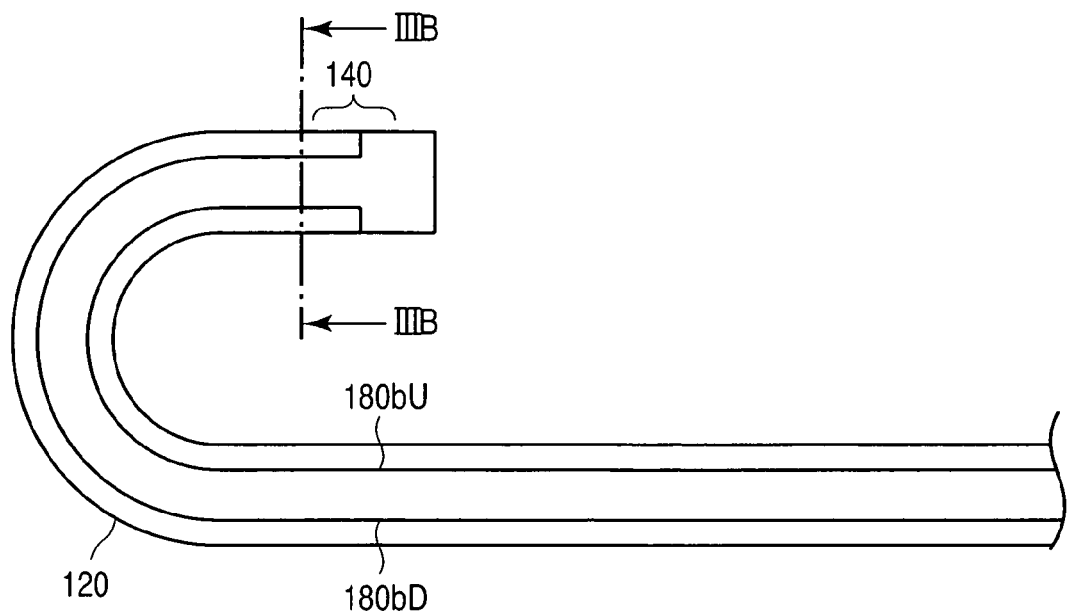
FIG. 3A is a diagram schematically showing a positional relationship between a shape of the insertion section and angle wires for explaining the shape of the insertion section and tensile force applied to the angle wires in the endoscopic system according to the first embodiment of the present invention.
Figure 3B:
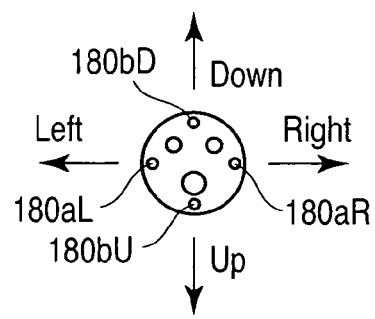
FIG. 3B is a diagram schematically showing a positional relationship of the angle wires with respect to the insertion section in the form of a cross-sectional view taken along IIIB-IIIB depicted in FIG. 3A for explaining the shape of the insertion section and tensile force applied to the angle wires in the endoscopic system according to the first embodiment of the present invention.

For example, as schematically shown in FIG. 3A and FIG. 3B, in a situation where the flexible tube section 120 is bent into the J-like shape in the UP direction, since a path of a lower wire 180*b*D of the UD angle wires 180*b* inserted in the flexible tube section 120 on the outer side of a central axis in a bent portion is longer than that when the flexible tube section 120 is straightened, the wire 180*b*D is pulled. Therefore, as compared with the shape that the flexible tube section 120 is straightened, tensile force applied to the lower wire 180*b*D is increased. On the other hand, a path length and tensile force of the RL angle wires 180*a* are the same as those in the shape that the flexible tube section 120 is straightened. Therefore, in this shape, when an operator rotates the operation knob to operate a bending state of the bending section 140, a magnitude of reaction force applied to the operator differs depending on rotation of the RL angle pulley 210 and rotation of the UD angle pulley 220. Therefore, for the operator, operational feeling differs depending on an operation of the RL angle pulley 210 and an operation of the UD angle pulley 220. Such a difference in operational feeling makes the operation of the bending section 140 difficult. Therefore, in this embodiment adjustment is carried out to reduce the tensile force of the wire 180*b*D in this case.

In this embodiment, the adjustment of the angle wires 180 having the above-described configuration is carried out as follows. That is, when approaching the gallbladder via the stomach in NOTES, the flexible tube section 120 is inserted through a similar path every time the surgical operation is conducted. When the same procedure is performed in this manner, how the flexible tube section 120 is bent is substantially the same every time the surgical operation is conducted.

In this embodiment explained below, a change in tensile force of the angle wires 180 caused by the bending of the flexible tube section 120 is adjusted. To determine an adjustment amount for the tensile force, this embodiment utilizes characteristics that how the flexible tube section 120 is bent is always substantially the same in every surgical operation. That is, a mode is previously set in accordance with an operative procedure or a target, and an adjustment value concerning the adjustment for the tensile force applied to the angle wires 180 based on how the flexible tube section 120 is bent is previously stored in accordance with each mode. Moreover, in this endoscopic system, the stored adjustment value is used to adjust the tensile force of the angle wires 180.

Figure 2B:
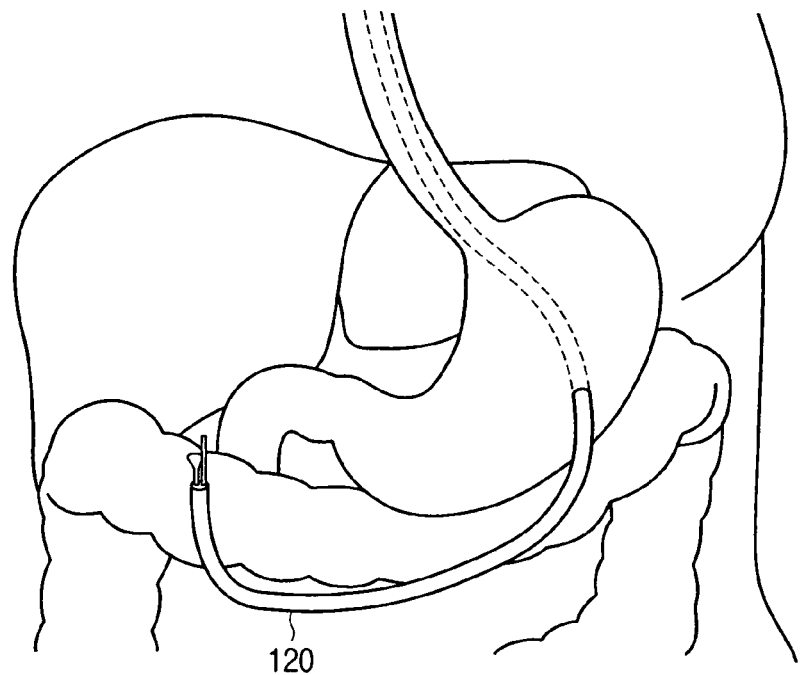
FIG. 2B is a schematic view showing an example of a shape of the insertion section when using the endoscopic system according to the first embodiment of the present invention in case of approaching a gallbladder in an abdominal cavity via a stomach in natural orifice transluminal endoscopic surgery.

In this embodiment, a situation where a curvature of bending of the flexible tube section 120 shown in FIG. 2A is relatively small is called a reversal (small) mode, a situation where a curvature of bending of the flexible tube section 120 is relatively large like NOTES shown in FIG. 2B is called a reversal (large) mode, a situation of approaching a sigmoid colon, a descending colon, a transverse colon, an ascending colon, and others is called a large intestine mode, respectively, and these modes are generically called a procedure mode.

Figures 4, 5:
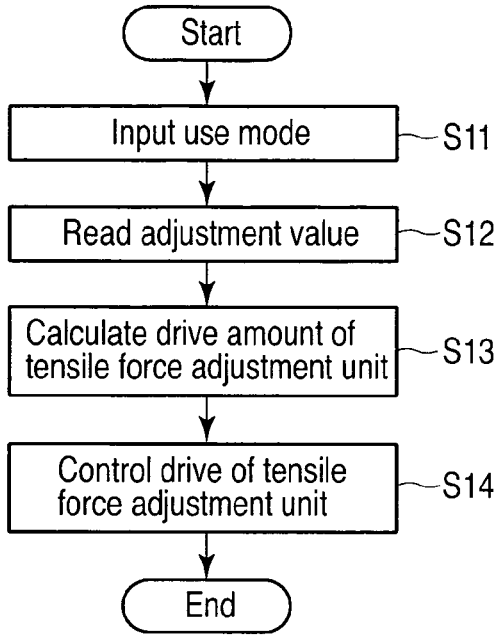
FIG. 4 is a flowchart for explaining an example of processing in a control unit in the endoscopic system according to the first embodiment of the present invention.
FIG. 5 is a diagram showing an example of information stored in a memory unit in the endoscopic system according to the first embodiment of the present invention.

Processing of the control unit 250 in the endoscopic system according to this embodiment will be described with reference to a flowchart depicted in FIG. 4. An operator first selects a desired procedure mode in accordance with a procedure that is being carried out and inputs the selected mode to the input unit 270. Here, as the input unit 270, it is possible to apply an input device having a configuration that buttons for specifying the reversal (small) mode, the reversal (large) mode, and the large intestine mode, respectively are provided. It is also possible to adopt a configuration that the input unit 270 is formed of a keyboard or a mouse and additionally includes a non-illustrated display and others. At a step S11, the control unit 250 receives an indication of the procedure mode used by the operator from the input unit 270.

At a step S12, the control unit 250 reads an adjustment value concerning the corresponding procedure mode in adjustment values concerning adjustment of tensile force of the angle wires stored in the memory unit 260 in accordance with the procedure mode input from the input unit 270. In the memory unit 260, for example, as shown in FIG. 5, a table concerned with the respective modes is provided, and the adjustment values concerning the adjustment of the tensile force of the angle wires 180 are stored in advance. As shown in this drawing, for example, a correspondent relationship of, e.g., increase/decrease levels of the tensile force for the angle wires 180 or adjustment levels of the RL tensile force adjustment unit 230 and the UD tensile force adjustment unit 240 with respect to each reference value are stored. The control unit 250 appropriately reads out an adjustment value in accordance with the procedure mode from these values and executes the adjustment.

At a step S13, the control unit 250 calculates a drive amount of the linear actuator 232 for moving the movable pulley 234 and the movable pulley 236 of the RL tensile force adjustment unit 230 and a drive amount of the linear actuator 242 for moving the movable pulley 244 and the movable pulley 246 of the UD tensile force adjustment unit 240 in accordance with the read wire tensile force adjustment value.

At a step S14, the control unit 250 controls drive of the linear actuator 232 and the linear actuator 242 based on the calculated drive amounts, thereby adjusting the tensile force of the angle wires 180.

Here, the RL tensile force adjustment unit 230 will be taken as an example to describe operations of the RL tensile force adjustment unit 230 and the UD tensile force adjustment unit 240. The movable pulley 234 and the movable pulley 236 are moved by the linear actuator 232. As shown in FIG. 6A, center positions of movable ranges of the movable pulley 234 and the movable pulley 236 are determined as a reference state. When decreasing the tensile force applied to the RL angle wires 180a is desired, the movable pulley 234 and the movable pulley 236 are moved to shorten paths of the angle wires 180 as shown in FIG. 6B. Contrarily, when increasing the tensile force applied to the RL angle wires 180a is desired, the movable pulley 234 and the movable pulley 236 are moved to extend the paths of the angle wires 180 as shown in FIG. 6C.

In this manner, the tensile force applied to the angle wires 180 is adjusted in accordance with positions of the movable pulley 234 and the movable pulley 236. It is to be noted that the linear actuators may be provided to the movable pulley 234 and the movable pulley 236, respectively so that these pulleys can be individually moved. When these pulleys can be individually moved, tensile force adjustment can be carried out with respect to each of the two RL angle wires 180a connected to one node ring. This configuration can be also applied to the UD tensile force adjustment unit 240.

Mechanisms of the RL tensile force adjustment unit 230 and the UD tensile force adjustment unit 240 are not restricted to configurations depicted in FIGS. 6A, 6B, and 6C, and any other configuration may be adopted if the tensile force of the angle wires 180 can be changed.

Figure 7:
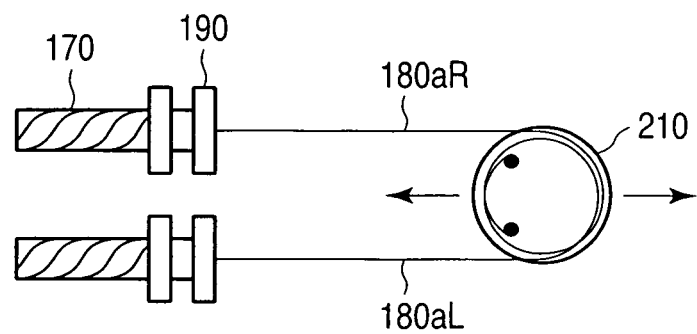
FIG. 7 is a diagram for explaining a first modification of the mechanism of the tensile force adjustment unit in the endoscopic system according to the first embodiment of the present invention.

As a first modification, as shown in FIG. 7, a non-illustrated movement mechanism that moves a shaft of the RL angle pulley 210 may be provided to effect movement so that a distance between the RL angle pulley 210 and each coil receiver 190 can be changed.

Figure 8:
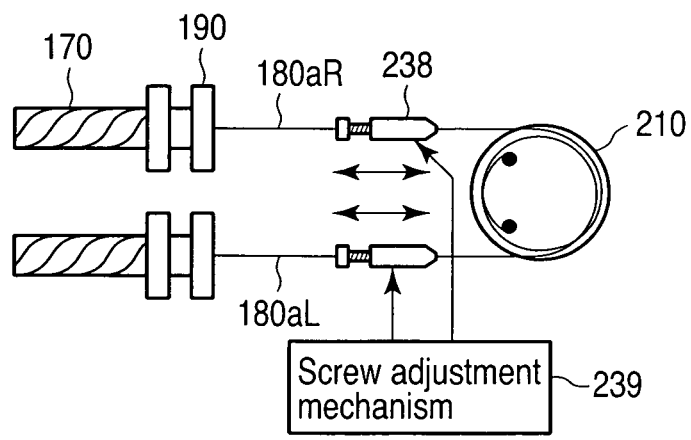
FIG. 8 is a diagram for explaining a second modification of the mechanism of the tensile force adjustment unit in the endoscopic system according to the first embodiment of the present invention.
Figure 9:
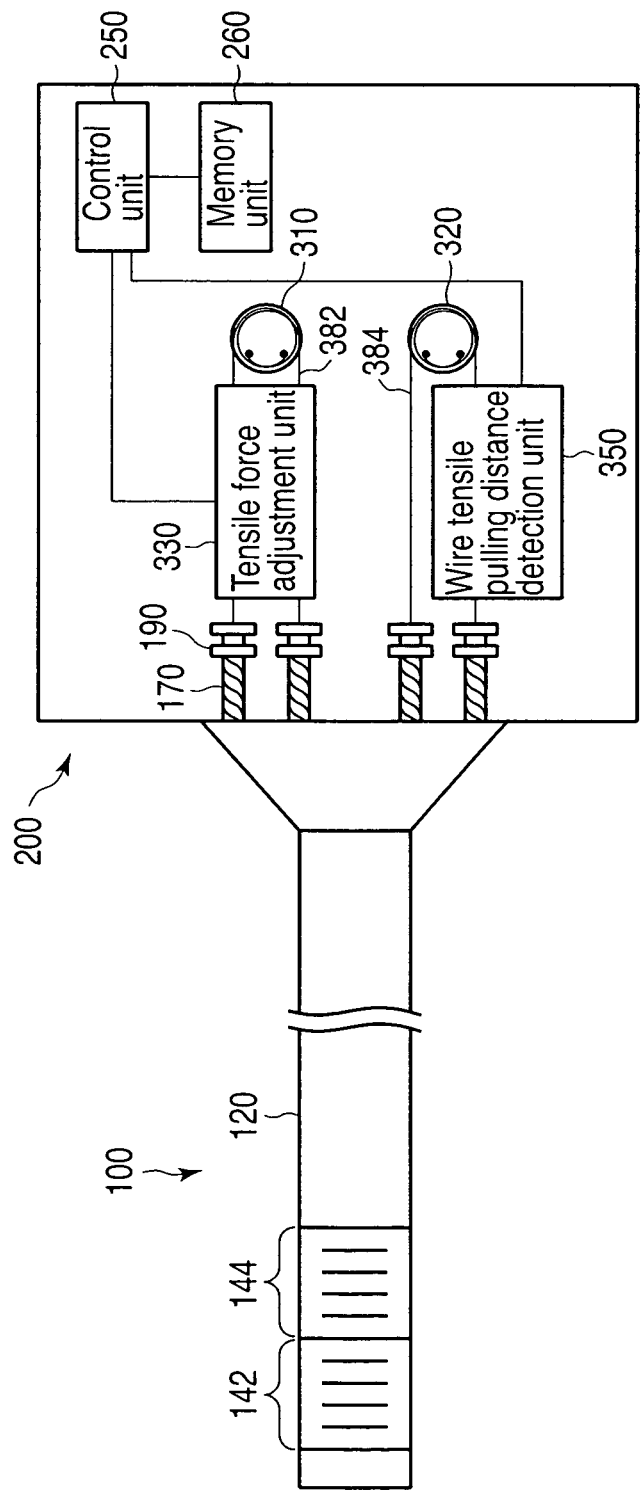
FIG. 9 is a diagram schematically showing an example of a configuration of an endoscopic system according to a second embodiment of the present invention.

Further, as a second modification, as shown in FIG. 8, adjustment screws 238 that change an entire length may be provided between the RL angle pulley 210 and the coil receivers 190 so that the adjustment screws can be utilized to adjust the tensile force of the RL angle wires 180a. That is, a screw adjustment mechanism 239 may rotate the adjustment screws 238 in accordance with a change in tensile force applied to the RL angle wires 180a to change the entire length, thereby adjusting the tensile force of the RL angle wires 180a.

According to the endoscopic system of this embodiment described above, the tensile force of the angle wires 180 can be adjusted in accordance with each procedure mode in accordance with an operative procedure or a target to eliminate a change in tensile force caused due to a bent shape of the insertion section. As a result, the operator can constantly perform the bending operation for the bending section 140 with the same operational feeling irrespective of the bent shape of the flexible tube section 120. Since the bending section 140 can have an expected bending angle (a bending amount) by an operation of the operator with the same operation feeling, this tensile force adjustment can exhibit the effect of realizing the more accurate operation of the bending section 140 without an uncomfortable feeling.

Furthermore, the RL angle pulley 210 and the UD angle pulley 220 according to this embodiment have been described as manual operation mechanisms that rotate when the operator rotates the operation knobs coupled with these pulleys. However, the present invention is not restricted to this configuration, and the wire tensile force adjustment mechanism according to this embodiment can be likewise used in, e.g., an endoscopic system having an electric operation mechanism that electrically rotates the RL angle pulley 210 and the UD angle pulley 220. In case of the electric operation mechanism is used, likewise, to accurately operate the bending section 140 to bend, when the tensile force applied to the angle wires 180 is changed, a control parameter concerning the operation of the electric operation mechanism have to be adjusted in accordance with this change. On the other hand, according to the endoscopic system having the wire tensile force adjustment mechanism of this embodiment, since the tensile force of the angle wires 180 is adjusted for each procedure mode in accordance with an operative procedure or a target to eliminate a change in tensile force caused due to a bent shape of the insertion section, the control parameter concerning the electric operation mechanism does not have to be adjusted in accordance with the tensile force of the angle wires 180. Therefore, the tensile force adjustment of the angle wires 180 according to this embodiment exhibits the effect of facilitating the control of the electric operation mechanism.

It is to be noted that the wire tensile force adjustment mechanism according to this embodiment is not restricted to use in an endoscope, and it can be likewise used in a flexible elongated manipulator that bends the bending section by pulling or loosening the wires, thereby obtaining the same effect.

[Second Embodiment]

A second embodiment will now be described. Here, in the second embodiment, a difference from the first embodiment will be described, and like reference numbers denote parts equal to those in the first embodiment to omit description thereof. An endoscopic system according to this embodiment is exemplified by a multistage bending endoscope that comprises joints including a first bending section 142 placed on a distal end side of an insertion section 100 and a second bending section 144 placed on a proximal end side of the first bending section 142.

In the multistage bending endoscope, wires reach angle pulleys through the joints. Therefore, when the multistage bending endoscope is bent, tensile force of an angle wire connected to a joint on the distal end side of the insertion section is affected by bending of other joints. That is, the tensile force of the angle wire connected to the joint on the distal end side is increased or decreased by bending of a joint on the proximal end side of this joint. That is, initial tensile force that defines first movement of the bending section with respect to a rotational angle of the pulley differs. This difference in initial tensile force makes an operational feeling of an operation knob different for an operator. Such a difference in operational feeling makes an accurate operation of the bending section difficult.

Since angle wires 180 configured to bend the first bending section 142 run through the second bending section 144, their tensile force varies depending on a bent shape such as a bending angle or a bending direction of the second bending section 144. Therefore, in this embodiment, tensile force of first angle wires 382 configured to drive the first bending section 142 is adjusted in accordance with the bent shape of the second bending section 144 arranged on the proximal end side. Here, in this embodiment, the bent shape of the second bending section 144 is acquired by detecting a moving distance of the second angle wires 384 configured to bend the second bending section 144.

One end of each of the pair of first angle wires 382 configured to bend the first bending, section 142 is wound around and fixed to a first bending pulley 310 in an operating section 200 like the first embodiment. Furthermore, the other end of each of the pair of first angle wires 382 is inserted into the insertion section 100 and fixed to a node ring of the first bending section 142. Likewise, one end of each of the pair of second angle wires 384 configured to bend the second bending section 144 is wound around and fixed to the second bending pulley 320, and the other end of the same is inserted into the insertion section 100 and fixed to a node ring of the second bending section 144.

In regard to the first angle wires 382, the same tensile force adjustment unit 330 as the RL tensile force adjustment unit 230 according to the first embodiment is arranged between coil receivers 190 and the first bending pulley 310. The tensile force adjustment unit 330 is connected to the control unit 250 like the first embodiment to adjust the tensile force of the first angle wires 382 under control of the control unit 250.

On the other hand, in regard to the second angle wires 384, a wire pulling distance detection unit 350 that detects a moving distance of the second angle wires 384 is arranged between the coil receivers 190 and the second bending pulley 320. The wire pulling distance detection unit 350 is, e.g., a linear encoder that detects a moving distance of the second angle wires 384. Moreover, for example, the wire pulling distance detection unit 350 may be a potentiometer that detects a rotational angle of the second bending pulley 320 that pulls and loosens the second angle wires 384. The wire pulling distance detection unit 350 outputs the detected moving distance of the second angle wires 384 to the control unit 250.

The control unit 250 reads necessary information from a memory unit 260 based on the moving distance of the second angle wires 384 input from the wire pulling distance detection unit 350 and calculates a value concerning adjustment of the tensile force of the first angle wires 382. The control unit 250 controls an operation of the tensile force adjustment unit 330 based on the calculated adjustment value.

In this manner, for example, the wire pulling distance detection unit 350 functions as a wire moving distance detection unit that detects a moving distance of the wires that transmit power to at least one of the bending sections.

An operation of the endoscopic system according to this embodiment will now be described with reference to a flowchart shown in FIG. 10. At a step S21, the control unit 250 acquires a moving distance of the second angle wires 384 from the wire pulling distance detection unit 350.

At a step S22, the control unit 250 reads a necessary adjustment value in adjustment values concerning adjustment for tensile force of the first angle wires 382 stored in the memory unit 260 in accordance with the acquired moving distance of the second angle wires 384. For example, as shown in FIG. 11, the memory unit 260 stores the adjustment values in connection with moving distances of the second angle wires 384. Further, in place of a table showing a relationship between each moving distance and each adjustment value of the second angle wires 384 like FIG. 11, a function representing such a relationship may be saved.

At a step S23, the control unit 250 calculates a drive amount of a mechanism in the tensile force adjustment unit 330 in accordance with the read adjustment value. For example, like the RL tensile force adjustment unit 230 in the first embodiment, when a mechanism including a movable pulley is provided, a drive amount of a linear actuator for moving this movable pulley is calculated.

At a step S24, the control unit 250 controls drive of the mechanism in the tensile force adjustment unit 330 based on the calculated drive amount, thereby adjusting the tensile force of the first angle wires 382.

According to this embodiment, a bent state of the second bending section 144 that changes the tensile force of the first angle wires 382 is detected by acquiring the moving distance of the second angle wires 384. When the tensile force of the first angle wires 382 is adjusted in accordance with the detected bent shape of the second bending section 144, the change in tensile force caused due to the bent shape of the second bending section 144 can be eliminated. As a result, an operator can always operate the first bending section 142 to bend with the same operational feeling irrespective of the bent shape of the second bending section 144. Since the first bending section 142 can have an expected bending angle (a bending amount) by the operation of the operator with the same operational feeling, this tensile force adjustment exhibits the effect of realizing the more accurate operation of the first bending section 142 without an uncomfortable feeling.

It is to be noted that, in this embodiment, an input unit 270 may be provided so that the tensile force of each of the first angle wires 382 and the second angle wires 384 can be adjusted on the basis of a bent state of a flexible tube section 120 determined for each procedure mode in accordance with an operative procedure or a target like the first embodiment. In this case, as to the tensile force adjustment of the first angle wires 382, like the first embodiment, the tensile force adjustment is carried out for each procedure mode with reference to, e.g., such information as depicted in FIG. 5, and then the tensile force adjustment based on a moving distance of the second angle wires 384 according to this embodiment is performed. That is, an adjustment value concerning the adjustment for the tensile force of the first angle wires 382 is a sum of an adjustment value based on the procedure mode and an adjustment value based on the moving distance of the second angle wires 384. In this case, for example, the input unit 270 and the wire pulling distance detection unit 350 function as a shape acquiring unit.

Further, like the first embodiment, a first bending pulley 310 and a second bending pulley 320 may be, e.g., electric operation mechanisms rotated by electric power. Even in this case, since the tensile force of the first angle wires 382 (including the second angle wires 384 when performing the tensile force adjustment according to a procedure mode) is adjusted, a control parameter concerning the electric operation mechanism does not have to be adjusted in accordance with the tensile force of the first angle wires 382 (and the second angle wires 384). Therefore, the tensile force adjustment according to this embodiment exhibits the effect of facilitating control of the electric operation mechanism.

Furthermore, each of the first bending section 142 and the second bending section 144 is not restricted to a configuration including one bending pulley like this embodiment, and it may have a configuration including two bending pulleys to enable bending in four directions, i.e., up, down, left, and right directions.

Moreover, the bending sections are not restricted to the two bending sections, i.e., the first bending section 142 and the second bending section 144, and three or more bending sections may be provided. In this case, like this embodiment, the bending section on the distal end side can be configured in such a manner that tensile force of the driving angle wires can be adjusted on the basis of bent states of the bending sections provided on the proximal end side of this bending section.

In any case, this endoscopic system has the same effect as that of this embodiment.

It is to be noted that the tensile force adjustment mechanism for the wires according to this embodiment is not restricted to the endoscope, and it can be likewise used in a flexible elongated manipulator that bends the bending sections by pulling and loosening the wires like the endoscope, thereby obtaining the same effect.

[Third Embodiment]

Figure 12:
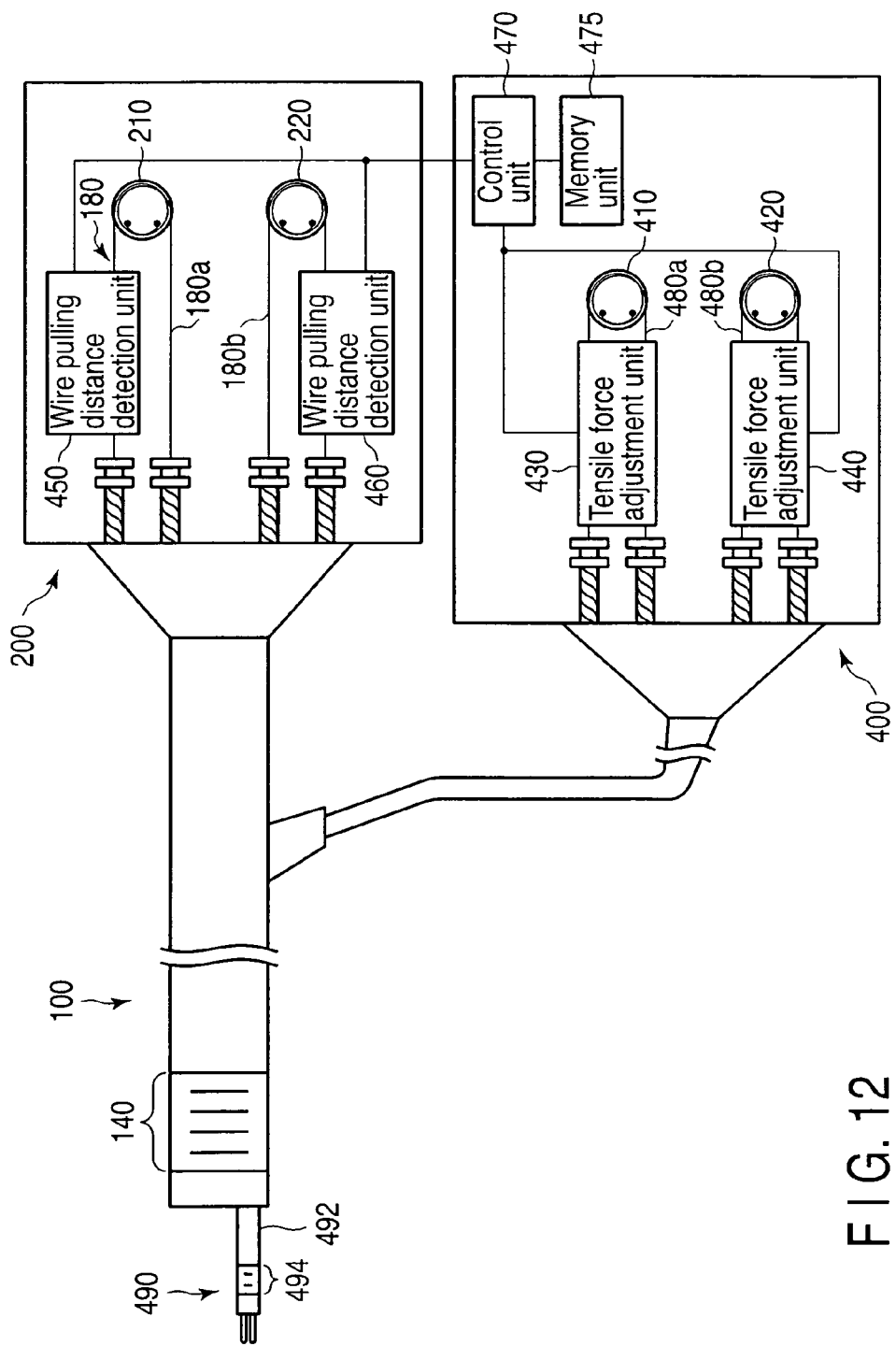
FIG. 12 is a diagram schematically showing an example of a configuration of an endoscopic system according to a third embodiment of the present invention.

A third embodiment according to the present invention will now be described hereinafter. Here, in the third embodiment, a difference from the first embodiment will be described, and like reference numbers denote parts equal to those in the first embodiment, thereby omitting description thereof. As schematically shown in FIG. 12, the endoscopic system according to this embodiment is an endoscopic system having a configuration that a manipulator is inserted in a forceps opening of an insertion section 100 of an endoscope. Basic mechanisms of the manipulator are equal to the structures in the endoscope except that an insertion section 490 has a small diameter in order to be inserted into the forceps opening of the endoscope. A bending section 494 is provided at a distal end of the insertion section 490 of the manipulator. This bending section 494 is bent by pulling and loosening RL angle wires 480a by an RL angle pulley 410 and pulling and loosening UD angle wires 480b by a UD angle pulley 420.

An adjustment mechanism for tensile force of the angle wires according to the present invention is provided in this manipulator. Tensile force of the RL angle wires 480a and that of the UD angle wires 480b vary depending on a bent shape of a bending section 140 of the endoscope in which these wires are inserted. In the endoscopic system according to this embodiment, the tensile force of the RL angle wires 480a and that of the UD angle wires 480b are adjusted in accordance with a bent shape of the bending section 140 of the endoscope to improve an operational feeling of the bending section 494 of the manipulator for an operator.

The insertion section 490 of the manipulator comprises an elongated flexible tube section 492 and the bending section 494 provided at a distal end of this flexible tube section 492. Furthermore, like the endoscope, the pair of RL angle wires 480a configured to drive the bending section 494 in a right-left direction and the pair of UD angle wires 480b configured to drive the bending section 494 in an up-down direction are inserted into the insertion section 490.

One end of each of the pair of RL angle wires 480a is wound around and fixed to the RL angle pulley 410 in an operating section 400 of the manipulator. Moreover, the other end of each of the pair of RL angle wires 480a is fixed to a node ring of the bending section 494. Likewise, one end of each of the pair of UD angle wires 480b is wound around and fixed to the UD angle pulley 420 in the operating section 400 of the manipulator, and the other end of the same is fixed to a node ring of the bending section 494.

The same RL tensile force adjustment unit 430 as the RL tensile force adjustment unit 230 according to the first embodiment is provided to the RL angle wires 480a, and the same UD tensile force adjustment unit 440 is provided to the UD angle wires 480b. The RL tensile force adjustment unit 430 and the UD tensile force adjustment unit 440 are connected to a control unit 470 of the manipulator. The RL tensile force adjustment unit 430 and the UD tensile force adjustment unit 440 drive to adjust tensile force of the RL angle wires 480a and that of the UD angle wires 480b under control of the control unit 470, respectively.

On the other hand, in the endoscope according to the present invention, the same RL wire pulling distance detection unit 450 as the wire pulling distance detection unit 350 in the second embodiment is provided to the RL angle wires 180a configured to bend the bending section 140 of the endoscope. Likewise, a UD wire pulling distance detection unit 460 is provided to the UD angle wires 180b. The RL wire pulling distance detection unit 450 and the UD wire pulling distance detection unit 460 are connected to the control unit 470 to output moving distances of the RL angle wires 180a and the UD angle wires 180b to the control unit 470, respectively.

The control unit 470 calculates a value concerning adjustment of tensile force of each of the RL angle wires 480a and the UD angle wires 480b based on inputs from the RL wire pulling distance detection unit 450 and the UD wire pulling distance detection unit 460 by utilizing information stored in a memory unit 475. The control unit 470 also controls the RL tensile force adjustment unit 430 and the UD tensile force adjustment unit 440 to adjust the tensile force of each of the RL angle wires 480a and the UD angle wires 480b.

In this manner, the insertion section 100 functions as, e.g., a flexible elongated endoscope insertion section, the bending section 140 functions as, e.g., an endoscope bending section, the RL angle wires 180a and the UD angle wires 180b function as, e.g., endoscope wires configured to bend the endoscope bending section, the RL wire pulling distance detection unit 450 and the UD wire pulling distance detection unit 460 function as, e.g., manipulator shape acquiring units, the insertion section 490 functions as, e.g., a manipulator, the RL angle wires 480a and the UD angle wires 480b function as, e.g., manipulator wires configured to transmit power for bending the manipulator bending section, the RL tensile force adjustment unit 430 and the UD tensile force adjustment unit 440 function as, e.g., manipulator adjustment units configured to adjust tensile force applied to the manipulator wires, the memory unit 475 functions as, e.g., a memory unit that stores information indicative of a relationship between a shape of the manipulator and adjustment values for driving the manipulator adjustment units in case of this shape of manipulator, and the control unit 470 functions as, e.g., a control unit that determines an adjustment value based on a shape of the manipulator acquired by the manipulator shape acquiring units and information stored in the memory unit and controls the manipulator adjustment unit based on the adjustment value.

Figures 13, 14:
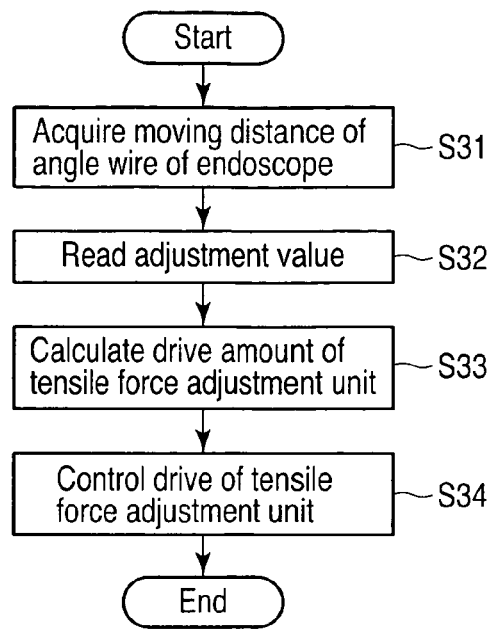
FIG. 13 is a flowchart for explaining an example of processing in a control unit of the endoscopic system according to the third embodiment of the present invention.
FIG. 14 is a diagram showing an example of information stored in a memory unit of the endoscopic system according to the third embodiment of the present invention.

An operation of the manipulator according to this embodiment will now be described with reference to a flowchart shown in FIG. 13.

At a step S31, the control unit 470 acquires moving distances of the RL angle wires 180a and the UD angle wires 180b of the endoscope from the RL wire pulling distance detection unit 450 and the UD wire pulling distance detection unit 460.

At a step S32, the control unit 470 reads necessary adjustment values in adjustment values concerning adjustment of tensile force of each of the RL angle wires 480a and the UD angle wires 480b stored in the memory unit 475 in accordance with the acquired moving distances of the RL angle wires 180a and the UD angle wires 180b. For example, as shown in FIG. 14, the memory unit 475 stores the adjustment values concerning the adjustment of the tensile force of each of the RL angle wires 480a and the UD angle wires 480b of the manipulator in connection with the moving distances of the RL angle wires 180a and the UD angle wires 180b of the endoscope. For example, as shown in FIG. 14, an upper side in each column represents an adjustment value concerning the adjustment of the tensile force of the RL angle wires 480a, and a lower side in the same presents an adjustment value concerning the adjustment of the tensile force of the UD angle wires 180b. Further, in place of the table showing the relationships between moving distances of the RL angle wires 180a and the UD angle wires 180b and adjustment values for the RL angle wires 480a and the UD angle wires 480b, a function representing such relationships may be saved.

At a step S33, the control unit 470 calculates drive amounts of mechanisms in the RL tensile force adjustment unit 430 and the UD tensile force adjustment unit 440 in accordance with the read adjustment values.

At a step S34, the control unit 470 controls drive of the mechanisms in the RL tensile force adjustment unit 430 and the UD tensile force adjustment unit 440 of the manipulator based on the calculated drive amounts, thereby adjusting the tensile force of each of the RL angle wires 480a and the UD angle wires 480b of the manipulator.

According to this embodiment, a bent shape of the bending section 140 that can be a cause of a change in the tensile force of each of the RL angle wires 480a and the UD angle wires 480b of the manipulator is acquired by detecting moving distances of the RL angle wires 180a and the UD angle wires 180b of the endoscope, and the tensile force of each of the RL angle wires 480a and the UD angle wires 480b of the manipulator can be adjusted in accordance with the acquired bent shape of the bending section 140 of the endoscope. As a result, an operator can constantly bend the bending section 494 of the manipulator with the same operational feeling irrespective of a bent shape of the bending section 140 of the endoscope without regard to this shape. Since the bending section 494 of the manipulator can have an expected bending angle by an operation of the operator with the same operational feeling, this tensile force adjustment can exhibit the effect of realizing the more accurate operation of the bending section 494 without an uncomfortable feeling.

It is to be noted that, in this embodiment, the input unit 270 may be provided like the first embodiment so that tensile force of each of the RL angle wires 480a and the UD angle wires 480b of the manipulator can be adjusted on the basis of a bent state of the flexible tube section 120 in each procedure mode in accordance with an operative procedure or a target. In this case, in regard to the tensile force adjustment of the RL angle wires 480a and the UD angle wires 480b of the manipulator, like the first embodiment, the tensile force adjustment based on a procedure mode is carried out, and then the tensile force adjustment based on moving distances of the RL angle wires 180a and the UD angle wires 180b of the endoscope according to this embodiment is performed. That is, the adjustment value concerning the tensile force adjustment of the RL angle wires 480a and the UD angle wires 480b is a sum of an adjustment value based on the procedure mode and an adjustment value based on moving distances of the RL angle wires 180a and the UD angle wires 180b of the endoscope. In this case, for example, the input unit 270, the RL wire pulling distance detection unit 450, and the UD wire pulling distance detection unit 460 function as a shape acquiring unit. Even in this case, the endoscopic system exhibits the same effect as that of this embodiment.

Further, like the first embodiment, the RL angle pulley 410 and the UD angle pulley 420 may be, e.g., electric operation mechanisms that are rotated by electric power. In this case, likewise, since the tensile force of each of the RL angle wires 480a and the UD angle wires 480b is adjusted, a control parameter concerning the electric operation mechanisms in accordance with the tensile force of the RL angle wires 480a and the UD angle wires 480b does not have to be adjusted. Therefore, the tensile force adjustment according to this embodiment exhibits the effect of facilitating the control of the electric operation mechanisms.

[Fourth Embodiment]

A fourth embodiment according to the present invention will now be described. Here, in the fourth embodiment, a difference from the first embodiment will be described, and like reference numbers denote parts equal to those in the first embodiment, thereby omitting a description thereof. An endoscopic system according to this embodiment is combined with a system that can acquire a shape of an endoscope.

In this embodiment, as shown in a schematic view of FIG. 15, the system is combined with an endoscope insertion shape observation apparatus (an endoscope position detection unit; UPD) 550. A flexible tube section 120 includes magnetic coils 555. The UPD 550 receives magnetism generated from the magnetic coils 555 by a non-illustrated antenna provided in the UPD 550 to calculate a shape of the flexible tube section 120. The UPD 550 outputs the calculated shape of the flexible tube section 120 of an endoscope to a control unit 250 of the endoscope. It is to be noted that the UPD is disclosed in, e.g., Jpn. Pat. Appln. KOKAI Publication No. 2000-79087.

Further, the present invention is not restricted to the UPD 550, and this unit may be substituted by an apparatus that utilizes, e.g., an X-ray apparatus to acquire a shape of the flexible tube section 120.

The control unit 250 of the endoscope reads information concerning tensile force adjustment of angle wires 180 from a memory unit 260 based on the shape of the flexible tube section 120 input from the UPD 550, uses this information to perform arithmetic processing, and thereby controls operations of an RL tensile force adjustment unit 230 and a UD tensile force adjustment unit 240.

In this manner, each magnetic coil 555 functions as, e.g., an indicator arranged in an insertion section, and the UPD 550 functions as, e.g., an insertion shape observation apparatus that acquires a shape of the insertion section in a contactless manner.

Figures 16, 17:
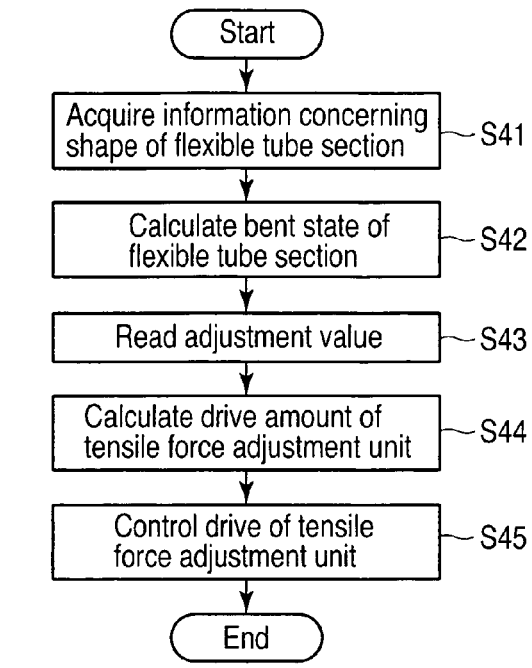
FIG. 16 is a flowchart for explaining an example of processing in a control unit in the endoscopic system according to the fourth embodiment of the present invention.
FIG. 17 is a diagram showing an example of information stored in a memory unit of the endoscopic system according to the fourth embodiment of the present invention.

An operation of a manipulator according to the embodiment will now be described with reference to a flowchart shown in FIG. 16.

At a step S41, the control unit 250 acquires information concerning a shape of the flexible tube section 120 from the UPD 550.

At a step S42, the control unit 250 calculates a bending direction, a curvature, and others of each portion of the flexible tube section from the acquired information concerning the shape of the flexible tube section 120.

At a step S43, the control unit 250 reads necessary adjustment values in adjustment values concerning tensile force adjustment of wires stored in the memory unit 260 in accordance with the bending directions, the curvatures, and others of the flexible tube section 120. For example, as shown in FIG. 17, the memory unit 260 stores values concerning the adjustment of the tensile force of each of the RL angle wires 180a and the UD angle wires 180b in connection with bending amounts of the flexible tube section 120 in an RL direction and a UD direction. For example, as shown in FIG. 17, an upper side in each column represents an adjustment value concerning the adjustment of the tensile force of the RL angle wires 180a, and a lower side in the same presents an adjustment value concerning the adjustment of the tensile force of the UD angle wires 180b. Alternatively, a function representing such relationships may be saved.

At a step S44, the control unit 250 calculates drive amounts of mechanisms in the RL tensile force adjustment unit 230 and the UD tensile force adjustment unit 240 in accordance with the read adjustment values.

At a step S45, the control unit 250 controls drive of the mechanisms in the RL tensile force adjustment unit 23 and the UD tensile force adjustment unit 240 based on the calculated drive amount, and adjusts tensile force of each of the RL angle wires 180a and the UD angle wires 180b.

According to this embodiment, a shape of the flexible tube section 120 that changes the tensile force of each of the RL angle wires 180a and the UD angle wires 180b of the endoscope is acquired by using each magnetic coil 555 and the UPD 550, and the tensile force of each of the RL angle wires 180a and the UD angle wires 180b can be adjusted in accordance with the shape of the flexible tube section 120. As a result, an operator can constantly bend the bending section 140 with the same operational feeling irrespective of a bent shape of the flexible tube section 120 of the endoscope without regard to this shape. Since the bending section 140 can have an expected bending angle (an bending amount) by an operation of the operator with the same operational feeling, this tensile adjustment can exhibit the effect of realizing the more accurate operation of the bending section 140 without an uncomfortable feeling.

Furthermore, like the first embodiment, each of the RL angle pulley 210 and the UD angle pulley 220 may be, e.g., an electric operation mechanism that is rotated by electric power. Even in this case, since tensile force of each of the RL angle wires 180a and the UD angle wires 180b is adjusted, a control parameter concerning the electric operation mechanism in accordance with the tensile force of each of the RL angle wires 180a and the UD angle wires 180b does not have to be adjusted. Therefore, the tensile force adjustment according to this embodiment can exhibit the effect of facilitating control of the electric operation mechanism.

It is to be noted that the tensile force adjustment mechanism for the wires according to this embodiment is not restricted to the endoscope, and it can be likewise used in a manipulator that has a flexible elongated shape and bends the bending section by pulling and loosening the wires, thereby obtaining the same effect.

[Fifth Embodiment]

A fifth embodiment according to the present invention will now be described. Here, in the fifth embodiment, a difference from the first embodiment will be described, and like reference numbers denote parts equal to those in the first embodiment, thereby omitting description thereof. An endoscopic system according to this embodiment is combined with an endoscope comprising an overtube configured to bend a flexible tube section 120 of the endoscope by an operation of an operator.

Figure 18:
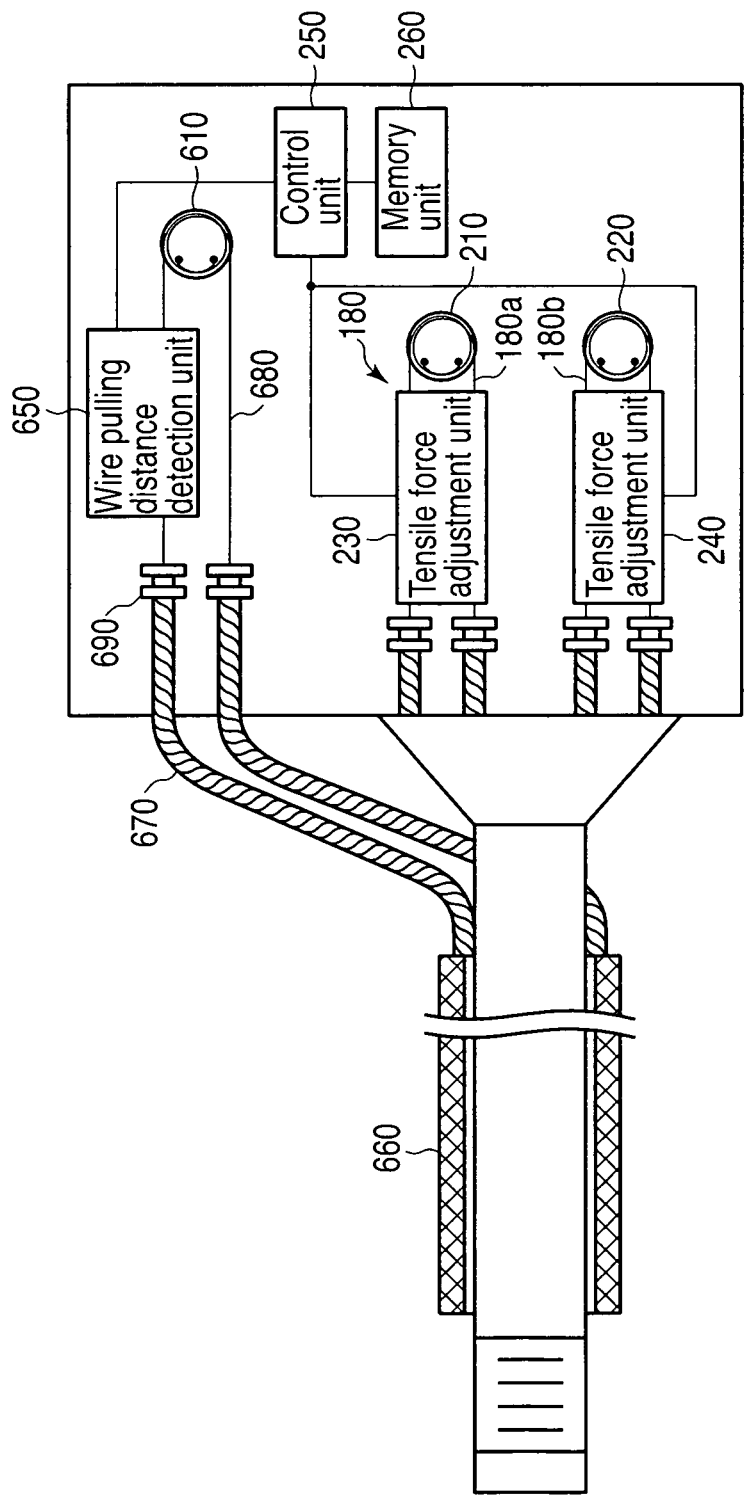
FIG. 18 is a diagram schematically showing an example of a configuration of an endoscopic system according to a fifth embodiment of the present invention.

In this embodiment, for example, as schematically shown in FIG. 18, an overtube 660 is provided on a circumferential portion of the flexible tube section 120. Like a bending section 140 of the endoscope, coil pipes 670 are inserted in the overtube 660, and the coil pipes 670 are extended to an operating section 200 and fixed to the operating section 200 by coil receivers 690. Overtube wires 680 are inserted in the coil pipes 670. The overtube wires 680 are wound around and fixed to an overtube pulley 610 in the operating section 200. Therefore, when the operator rotates a non-illustrated angle knob connected to the overtube pulley 610, the overtube pulley 610 rotates to pull and loosen the overtube wires 680. As a result, the flexible tube section 120 of the endoscope in the overtube 660 is bent.

In this embodiment, the same wire pulling distance detection unit 650 as the wire pulling distance detection unit 350 according to the second embodiment is arranged between the coil receiver 690 and the overtube pulley 610 to acquire a moving distance of the overtube wires 680. It is to be noted that this wire pulling distance detection unit 650 may be, e.g., a linear encoder that detects a moving distance of the overtube wires 680 or a potentiometer that detects a rotational angle of the overtube pulley 610 as described in the second embodiment. The wire pulling distance detection unit 650 outputs the detected moving distance of the overtube wires 680 to a control unit 250.

The control unit 250 reads an adjustment value concerning tensile force adjustment of RL angle wires 180a and UD angle wires 180b based on the moving distance of the overtube wires 680 input from the wire pulling distance detection unit 650 and executes arithmetic processing by using the read adjustment value to control operations of the RL tensile force adjustment unit 230 and the UD tensile force adjustment unit 240.

In this manner, the overtube 660 functions as, e.g., an overtube that covers the circumferential surface of the insertion section and bends the insertion section, the overtube wires 680 function as, e.g., tube wires that transmit power to the overtube, and the wire pulling distance detection unit 650 functions as, e.g., a tube wire moving distance detection unit that detects a moving distance of the tube wires as a shape acquiring unit.

An operation of a manipulator according to the embodiment will now be described with reference to a flowchart shown in FIG. 19.

At a step S51, the control unit 250 acquires a moving distance of the overtube wires 680 from the wire pulling distance detection unit 650.

At a step S52, the control unit 250 reads a necessary adjustment value in adjustment values concerning tensile force adjustment of the wires stored in a memory unit 260 in accordance with the acquired moving distance of the overtube wires 680. When the overtube wire 680 has wires for bending in an RL direction and wires for bending in a UD direction and the wire pulling distance detection unit 650 acquires respective amounts of displacement, for example, as shown in FIG. 20, the memory unit 260 stores adjustment values concerning tensile force adjustment of the RL angle wires 180a and the UD angle wires 180b in connection with moving distances of the overtube wires 680. For example, as shown in FIG. 20, it is assumed that an upper side in each column represents an adjustment value concerning tensile force adjustment of the RL angle wires 180a, and a lower side in the same represents an adjustment value concerning tensile force adjustment of the UD angle wires 180b. Alternatively, a function representing the same relationship as these values may be stored.

At a step S53, the control unit 250 calculates a drive amount of a mechanism in the tensile force adjustment unit 330 in accordance with a read adjustment value. For example, when the same mechanism as the RL tensile force adjustment unit 230 in the first embodiment is provided, a drive amount of the linear actuator 232 for moving the movable pulley 234 is calculated.

At a step S54, the control unit 250 controls drive of mechanisms in the RL tensile force adjustment unit 230 and the UD tensile force adjustment unit 240 based on the calculated drive amount, thereby adjusting the tensile force of the angle wires 180.

According to this embodiment, a bent shape of the flexible tube section 120 that changes the tensile force of the angle wires 180 is detected by acquiring a moving distance of the overtube wires 680, and the tensile force of the angle wires 180 can be adjusted on the basis of the detected bent state of the flexible tube section 120. As a result, an operator can always naturally operate the bending section 140 to bend with the same operational feeling irrespective of the bent state of the flexible tube section 120. Since the bending section 140 can have an expected bending angle (a bending amount) by the operation of the operator with the same operational feeling, this tensile force adjustment exhibits the effect of realizing the more accurate operation of the bending section 140 without an uncomfortable feeling.

Further, like the first embodiment, each of the RL angle pulley 210 and the UD angle pulley 220 may be, e.g., an electric operation mechanism rotated by electric power. In this case, since tensile force of the angle wires 180 is adjusted, adjustment of a control parameter concerning the electric operation mechanism in accordance with the tensile force of the angle wires 180 does not have to be carried out. Therefore, the tensile force adjustment according to this embodiment exhibits the effect of facilitating control of the electric operation mechanism.

It is to be noted that the tensile force adjustment mechanism of the wires according to this embodiment is not restricted to the endoscope, and it can be likewise used in a manipulator that has a flexible elongated shape and bends the bending section by pulling and loosening the wires, thereby obtaining the same effect.

[Combinations of Respective Embodiments]

The second embodiment to the fifth embodiment can be combined. For example, the multistage bending endoscope according to the second embodiment can be combined with the manipulator according to the third embodiment. In this case, as shown in FIG. 21, first wire pulling distance detection unit 352 and a second wire pulling distance detection unit 354 detect moving distances of first angle wires 382 and second angle wires 384 configured to bend a first bending section 142 and a second bending section 144, respectively. The first wire pulling distance detection unit 352 and the second wire pulling distance detection unit 354 output the detected moving distances of the first angle wires 382 and the second angle wires 384 to a control unit 470 of a manipulator. The control unit 470 calculates a value concerning tensile force adjustment of RL angle wires 480a and UD angle wires 480b of the manipulator while making reference to information stored in a memory unit 475. Further, an RL tensile force adjustment unit 430 and a UD tensile force adjustment unit 440 are controlled to adjust tensile force of each of the RL angle wires 480a and the UD angle wires 480b. In this case, for example, the first wire pulling distance detection unit 352 and the second wire pulling distance detection unit 354 function as wire moving distance detection units which are manipulator shape acquiring unit.

Figure 22:
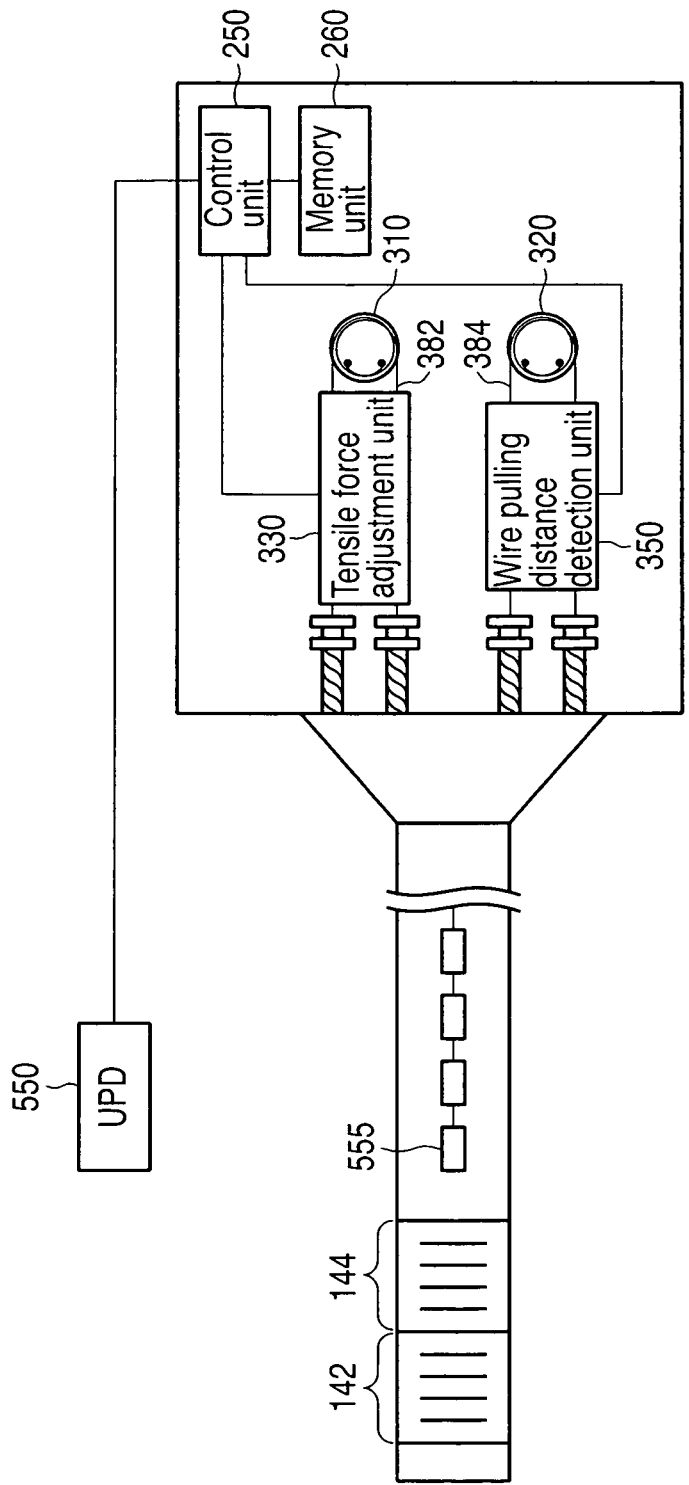
FIG. 22 is a diagram schematically showing an example of a configuration of an endoscopic system according to an embodiment that is a combination of the second embodiment and the fourth embodiment of the present invention.

Furthermore, the multistage bending endoscope according to the second embodiment can be combined with the UPD according to the fourth embodiment. In this case, as schematically shown in FIG. 22, a flexible tube section 120 of an endoscope includes magnetic coils 555, and a UPD 550 detects magnetism from the magnetic coils 555 and outputs information concerning a shape of the flexible tube section 120 to a control unit 250. Moreover, a wire pulling distance detection unit 350 detects a moving distance of second angle wires 384 and outputs this moving distance to the control unit 250. The control unit 250 calculates a value concerning adjustment of tensile force applied to first angle wires 382 from a shape of the flexible tube section 120 input from the UPD 550 and a moving distance of the second angle wires 384 input from the wire pulling distance detection unit 350 while making reference to information stored in a memory unit 260. In this case, in regard to the tensile force adjustment of the first angle wires 382, like the fourth embodiment, the tensile force adjustment is carried out based on the shape of the flexible tube section 120 with reference to such information as depicted in FIG. 17, and then the tensile force adjustment is performed based on the moving distance of the second angle wires 384 according to the second embodiment. That is, the adjustment value concerning the tensile force adjustment of the first angle wires 382 is a sum of an adjustment value based on an input from the UPD 550 and an adjustment value based on a moving distance of the second angle wires 384. The control unit 250 controls a tensile force adjustment unit 330 to adjust the tensile force of the first angle wires 382. In this case, the UPD 550 functions as, e.g., an insertion shape observation apparatus which is a manipulator shape acquiring unit, and the wire pulling distance detection unit 350 functions as, e.g., a wire moving distance detection unit.

Further, the multistage bending endoscope according to the second embodiment can be combined with the overtube according to the fifth embodiment 5. In this case, as shown in FIG. 23, a flexible tube section 120 of an endoscope has an overtube 660, and overtube wires 680 configured to bend the overtube 660 and a wire pulling distance detection unit 650 configured to detect tensile force of the wires are provided. The wire pulling distance detection unit 650 outputs a moving distance of the overtube wires 680 concerning a shape of a flexible tube section 120 to a control unit 250 like the fifth embodiment. Further, the wire pulling distance detection unit 350 detects a moving distance of second angle wires 384 and outputs the moving distance to the control unit 250. The control unit 250 calculates a value concerning adjustment of tensile force applied to first angle wires 382 from the moving distance of the overtube wires 680 input from the wire pulling distance detection unit 650 and the moving distance of the second angle wires 384 input from the wire pulling distance detection unit 350 while making reference to information stored in a memory unit 260. In this case, like the fifth embodiment, in regard to the tensile force adjustment of the first angle wires 382, for example, tensile force adjustment is performed based on an input from the wire pulling distance detection unit 650 with reference to such information as shown in FIG. 20, and then the tensile force adjustment based on the moving distance of the second angle wires 384 according to the second embodiment is effected. That is, the adjustment value concerning adjustment of the tensile force applied to the first angle wires 382 is a sum of an adjustment value based on an input from the wire pulling distance detection unit 650 and an adjustment value based on the moving distance of the second angle wires 384. Furthermore, the control unit 250 controls a tensile force adjustment unit 330 to adjust the tensile force of the first angle wires 382. In this case, for example, the wire pulling distance detection unit 650 and the wire pulling distance detection unit 350 function as a tube wire moving distance detection unit and a wire moving distance detection unit, respectively, which are manipulator shape acquiring units.

Figure 24:
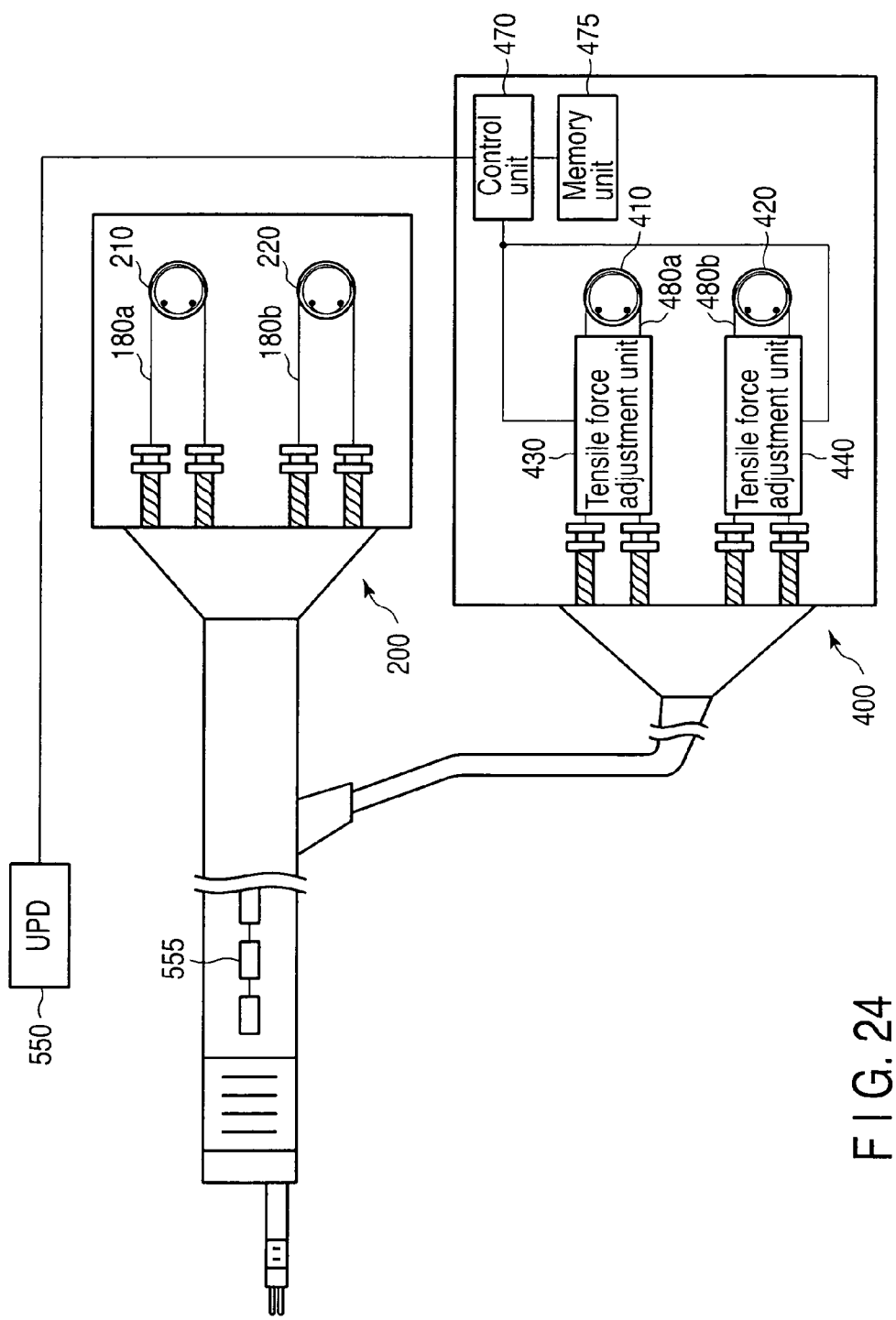
FIG. 24 is a diagram schematically showing an example of a configuration of an endoscopic system according to an embodiment that is a combination of the third embodiment and the fourth embodiment of the present invention.

Moreover, the manipulator according to the third embodiment can be combined with the UPD according to the fourth embodiment. In this case, as shown in FIG. 24, a flexible tube section 120 of an endoscope includes magnetic coils 555, and a UPD 550 detects magnetism from the magnetic coils 555 and outputs information concerning a shape of the flexible tube section 120 to a control unit 470 of a manipulator. The control unit 470 calculates a value concerning adjustment of tensile force of each of RL angle wires 480a and UD angle wires 480b like the third embodiment based on the shape of the flexible tube section 120 with reference to such information stored in a memory unit 475 as depicted in FIG. 17 like the fourth embodiment. The control unit 470 controls an RL tensile force adjustment unit 430 and a UD tensile force adjustment unit 440 to adjust the tensile force of each of the RL angle wires 480a and the UD angle wires 480b. In this case, for example, the UPD 550 functions as an insertion shape observation apparatus which is a manipulator shape acquiring unit.

Further, the manipulator according to the third embodiment can be combined with the overtube according to the fifth embodiment. In this case, as shown in FIG. 25, a flexible tube section 120 of an endoscope has an overtube 660, and it also has overtube wires 680 configured to bend the overtube 660 and a wire pulling distance detection unit 650 configured to detect tensile force of the wires. The wire pulling distance detection unit 650 outputs a moving distance of the overtube wires 680 concerning a shape of the flexible tube section 120 to a control unit 470 of the manipulator. The control unit 470 calculates a value concerning adjustment of tensile force of each of RL angle wires 480a and UD angle wires 480b based on the input moving distance of the overtube wire 680 and an input from the wire pulling distance detection unit 650 with reference to such information stored in memory unit 475 as depicted in FIG. 20 like the fifth embodiment. Furthermore, an RL tensile force adjustment unit 430 and a UD tensile force adjustment unit 440 are controlled to adjust the tensile force of each of the RL angle wires 480a and the UD angle wires 480b. In this case, for example, the wire pulling distance detection unit 650 functions as a tube wire moving distance detection unit which is a manipulator shape acquiring unit.

Moreover, it is possible to combine the multistage bending endoscope according to the second embodiment, the manipulator according to the third embodiment, and the UPD according to the fourth embodiment, or the overtube according to the fifth embodiment to each other. This example is the same as the above combinations. A shape of a flexible tube section 120 of a multistage bending endoscope is acquired by a UPD 550 or a wire pulling distance detection unit 650 of an overtube 660, and a control unit 470 of a manipulator calculates an adjustment value of tensile force of each of RL angle wires 480a and UD angle wires 480b in response to input of the acquired shape and controls an RL tensile force adjustment unit 430 and a UD tensile force adjustment unit 440 to adjust the tensile force of the RL angle wires 480a and the UD angle wires 480b.

In each of the combinations of the foregoing embodiments, the tensile force adjustment in the endoscopic system exhibits the effect of realizing the more accurate operation of the bending section without an uncomfortable feeling like the first to fifth embodiments. Additionally, when the pulley is, e.g., the electric operation mechanism, the effect of facilitating the control of the electric operation mechanism can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic system comprising:
a flexible elongated endoscope insertion section;
a manipulator wire configured to be pulled and loosened;
a manipulator which is inserted in the endoscope insertion section along a longitudinal direction of the endoscope insertion section to protrude from a distal end of the endoscope insertion section, and includes a manipulator bending section which is bent by the manipulator wire being pulled and loosened and a flexible elongated manipulator tubular section which is connected to a proximal end of the manipulator bending section, the manipulator wire being inserted in the manipulator tubular section;
a pulley configured to pull and loosen the manipulator wire so as to bend the manipulator bending section;
a manipulator adjustment unit comprising a movable member configured to move toward the manipulator wire and away from the manipulator wire, such that engagement of the movable member changes a length of a path of the manipulator wire so as to adjust a tensile force applied to the manipulator wire, the manipulator adjustment unit being separately provided from the pulley;
a manipulator shape information acquiring unit configured to acquire shape information indicating a shape of the manipulator tubular section, the shape of the manipulator tubular section including a bending angle or a curvature of the manipulator tubular section;

a memory unit which pre-stores correspondent information including a relationship between increase/decrease information and the shape information, the increase/decrease information indicating an increase/decrease in the tensile force due to the shape of the manipulator tubular section, the correspondent information being used to adjust the tensile force with keeping a same operational feeling irrespective of the shape of the manipulator tubular section; and a control unit configured to
- (i) obtain the increase/decrease information corresponding to the shape information acquired by the manipulator shape information acquiring unit with reference to the correspondent information stored in the memory unit,
- (ii) generate an adjustment signal configured to drive the manipulator adjustment unit based on the increase/decrease information to adjust the tensile force with keeping the same operational feeling irrespective of the shape of the manipulator tubular section so as to cancel the increase/decrease in the tensile force due to the shape of the manipulator tubular section, and
- (iii) output the adjustment signal to the manipulator adjustment unit.

2. The system according to claim 1, wherein
the endoscope insertion section includes an endoscope bending section and an endoscope wire configured to bend the endoscope bending section,
the shape information includes information indicative of a moving distance of the endoscope wire which indicates the shape of the manipulator tubular section, and
the manipulator shape information acquiring unit includes a wire moving distance detection unit configured to acquire the moving distance of the endoscope wire.

3. The system according to claim 2, wherein
the endoscope wire includes an RL angle wire and a UD angle wire,
the shape information includes information indicative of moving distances of the RL angle wire and the UD angle wire,
the correspondent information includes a relationship between increase/decrease information and the shape information indicative of the moving distances of both of the RL angle wire and the UD angle wire,
the wire moving distance detection unit is configured to acquire the moving distances of the RL angle wire and the UD angle wire, and
the manipulator adjustment unit is configured to change the length of the path of the manipulator wire in accordance with the moving distances of both the RL angle wire and the UD angle wire.

4. The system according to claim 1, wherein
the endoscope insertion section includes endoscope bending sections which are aligned along the longitudinal direction of the endoscope insertion section and endoscope wires configured to bend the endoscope bending sections,
the shape information includes information indicative of moving distances of the endoscope wires which indicates the shape of the manipulator tubular section, and
the manipulator shape information acquiring unit includes a wire moving distance detection unit configured to detect the moving distances of the endoscope wires.

5. The system according to claim 1, wherein
the manipulator shape information acquiring unit includes an insertion shape observation apparatus which utilizes an indicator arranged in the endoscope insertion section to acquire a shape of the endoscope insertion section in a contactless manner as the shape information, and
the shape information includes information indicating the shape of the endoscope insertion section which is configured to be acquired by the insertion shape observation apparatus.

6. The system according to claim 5, wherein
the indicator is a magnetic coil, and
the insertion shape observation apparatus is an apparatus configured to acquire the shape of the endoscope insertion section in the contactless manner based on magnetism generated from the magnetic coil.

7. The system according to claim 1, further comprising:
an overtube which covers a peripheral surface of the endoscope insertion section and is configured to bend the endoscope insertion section; and
a tube wire configured to transmit power that bends the overtube from an operating section arranged on a proximal end side of the endoscope insertion section to the overtube,
wherein the shape information includes information indicative of a moving distance of the tube wire which indicates the shape of the manipulator tubular section, and
the manipulator shape information acquiring unit includes a tube wire moving distance detection unit configured to detect the moving distance of the tube wire.

8. The system according to claim 7, wherein
the tube wire includes an RL angle wire and a UD angle wire,
the shape information includes information indicative of moving distances of the RL angle wire and the UD angle wire,
the correspondent information includes a relationship between increase/decrease information and the shape information indicative of the moving distances of both of the RL angle wire and the UD angle wire,
the tube wire moving distance detection unit is configured to acquire the moving distances of the RL angle wire and the UD angle wire, and
the manipulator adjustment unit is configured to change the length of the path of the manipulator wire in accordance with the moving distances of both the RL angle wire and the UD angle wire.

9. The system according to claim 1, wherein the manipulator adjustment unit is configured to change the length of the path of the manipulator wire so as to adjust the tensile force applied to the manipulator wire with keeping of a shape of the manipulator bending section irrespective of the shape of the manipulator tubular section.

10. The system according to claim 1, further comprising an actuator configured to move the movable member based on the adjustment signal from the control unit.

11. The system according to claim 10, wherein the manipulator adjustment unit comprises a pair of movable members, and the actuator is configured to move the pair of movable members.

12. The system according to claim 1, further comprising an angle controlling member connected to the manipulator wire and configured to pull and loosen the manipulator wire.

* * * * *